US008574315B2

(12) United States Patent
Reneker et al.

(10) Patent No.: US 8,574,315 B2
(45) Date of Patent: Nov. 5, 2013

(54) ELECTROSPUN STRUCTURES AND METHODS FOR FORMING AND USING SAME

(75) Inventors: Darrell Reneker, Akron, OH (US); Tao Han, Akron, OH (US); Daniel Smith, Stow, OH (US); Camden Ertley, Kent, OH (US); Joseph W. Reneker, Akron, OH (US)

(73) Assignee: The University of Akron, Akron, OH (US)

( * ) Notice: Subject to any disclaimer, the term of this patent is extended or adjusted under 35 U.S.C. 154(b) by 570 days.

(21) Appl. No.: 12/299,830

(22) PCT Filed: May 9, 2007

(86) PCT No.: PCT/US2007/011158
§ 371 (c)(1),
(2), (4) Date: Apr. 3, 2009

(87) PCT Pub. No.: WO2007/133570
PCT Pub. Date: Nov. 22, 2007

(65) Prior Publication Data
US 2010/0008994 A1    Jan. 14, 2010

Related U.S. Application Data

(60) Provisional application No. 60/798,928, filed on May 9, 2006, provisional application No. 60/849,213, filed on Oct. 4, 2006.

(51) Int. Cl.
A61K 9/14      (2006.01)
A61K 38/16     (2006.01)
A61K 39/395    (2006.01)
A61K 39/00     (2006.01)
A61K 38/43     (2006.01)
A61P 25/22     (2006.01)
A61P 25/26     (2006.01)
B32B 5/02      (2006.01)

(52) U.S. Cl.
USPC .... 977/904; 424/94.1; 424/130.1; 424/184.1; 424/489; 428/367; 428/368; 428/372; 977/906; 977/915; 977/931

(58) Field of Classification Search
USPC .......... 424/489, 130.1, 184.1, 94.1; 428/372, 428/367, 368; 264/10, 466; 502/159; 252/500, 519.33, 511; 514/12
See application file for complete search history.

(56) References Cited

U.S. PATENT DOCUMENTS 4,043,331 A      8/1977  Martin et al.
4,878,908 A     11/1989  Martin et al.
6,753,454 B1     6/2004  Smith et al.
2002/0081732 A1* 6/2002  Bowlin et al. ............... 435/446
2002/0082543 A1* 6/2002  Park et al. .................... 604/21
2003/0065355 A1* 4/2003  Weber ......................... 606/200
2003/0168756 A1* 9/2003  Balkus et al. ................ 264/10
2004/0241436 A1* 12/2004 Hsieh et al. .................. 428/361
2005/0037050 A1* 2/2005  Weber ......................... 424/426
2005/0158362 A1* 7/2005  Wheatley et al. ............ 424/426
2005/0191487 A1  9/2005  Magill et al.
2006/0021879 A1* 2/2006  Lin et al. ..................... 205/109
2006/0094320 A1* 5/2006  Chen et al. ................... 442/340
2008/0102192 A1* 5/2008  Johnson et al. .............. 427/2.1
2009/0075354 A1* 3/2009  Reneker et al. .............. 435/182

OTHER PUBLICATIONS

Dietzel et al., Electrospinning of polyme rnanofibers wtih specific surface chemistry, Polymer 43 (2002) p. 1025-1029 (5 pages total).*
Ettmayer et al., Lessons Learned from Marketed and Investigational Prodrugs, J. Med. Chem. (May 6, 2004) 47 (10) p. 2393-2404 (12 pages total).*
B. Testa, Prodrug research: futile or fertile?, Biochemical Pharmacology 68 (2004) 2097-2106 (10 pages).*
Dietzel et al., The Effect of processing variables on the morphology of electrospun nanofibers adn textiles, Polymer 43 (2001) p. 261-272 (12 pages).*
H. Fong, et al., Beaded nanofibers formed during electrospinning, Polymer 40 (2000), p. 4585-4592 (8 pages).*
D.H. Reneker, et al., Nanofiber garlands of polycaprolactone by electrospinning, Polymer 43 (2002) pp. 6785-6794 (10 pages).*
S.V. Diophode, et al., Nanofibers and spheres by polymerization of cyanoacrylate monomer, Polymer 47 (2006), 4328-4332 (5 pages).*
Cole Palmer, Disposable Glass Pasteur Pipettes (2 pages).*
Wenxia Liu, et al., Poly(meta-phenyl isophthalamide) nanofibers: Coating and post processing, J. Mater. Res. (Dec. 2002) vol. 17, No. 12, pp. 2306-3202 (7 pages).*
Liu et al. (Poly(meta-phenylene isophthalamide) nanofibers: Coating and post processing, J. Mater. Res. (Dec. 2002) vol. 17, No. 12, pp. 3206-3212).*

(Continued)

Primary Examiner — Ernst Arnold
(74) Attorney, Agent, or Firm — Renner Kenner Greive Bobak Taylor & Weber

(57) ABSTRACT

The present invention relates to structures that contain one or more fiber and/or nanofiber structures where such structures can be formed on a wide variety of structures or surfaces (e.g., asperities, flat surfaces, angled surface, hierarchical structures, etc.). In one embodiment, the present invention relates to a process for forming one or more fibers, nanofibers or structures made therefrom on a wide variety of structures or surfaces (e.g., asperities, flat surfaces, angled surface, hierarchical structures, etc.). In another embodiment, the present invention relates to a process for forming one or more fibers, nanofibers or structures made therefrom on a wide variety of structures or surfaces (e.g., asperities, flat surfaces, angled surface, hierarchical structures, etc.) where such fibers and/or structures are designed to sequester, carry and/or encapsulate one or more substances. In still another embodiment, the present invention relates to structures that contain one or more fiber and/or nanofiber structures on asperities where the nanofiber and/or fiber structures are designed to sequester, carry and/or encapsulate one or more substances.

4 Claims, 28 Drawing Sheets

(56) References Cited

OTHER PUBLICATIONS

Fong et al., Beaded nanofibers formed during electrospinning, Polymer 40 (1999) 4585-4592.*

Doiphode et al., Nanofibers and spheres by polymerization of cyanoacrylate monomer, Polymer 47 (2006) 4328-4332.*

Reneker et al., Nanofiber garlands of polycaprolactone by electrospinning, Polymer 43 (2002) 6785-6794.*

J.R. Smith, et al., Electrodes based on Magnelipahse titanium oxides:, Journal of Applied Electrochemistry, vol. 28 (1988), pp. 1021-1033, Reviews in Applied electrochemistry, No. 50.

* cited by examiner

ELECTROSPUN STRUCTURES AND METHODS FOR FORMING AND USING SAME

RELATED APPLICATION DATA

This application is a National Stage Application of PCT/US2007/011158, filed May 9, 2007, and claims priority to previously filed U.S. Provisional Patent Application Nos. 60/798,928, filed on May 9, 2006, entitled "Nanofiber Structures on Asperities For Sequestering, Carrying and Transferring Substances;" and 60/849,213, filed on Oct. 4, 2006, entitled "Bead-Coated Asperities Containing Useful Substances." Both of the above identified patent applications are hereby incorporated by reference in their entireties.

FIELD OF THE INVENTION

The present invention relates to structures that contain one or more fiber and/or nanofiber structures where such structures can be formed on a wide variety of structures or surfaces (e.g., asperities, flat surfaces, angled surface, hierarchical structures, etc.). In one embodiment, the present invention relates to a process for forming one or more fibers, nanofibers or structures made therefrom on a wide variety of structures or surfaces (e.g., asperities, flat surfaces, angled surface, hierarchical structures, etc.). In another embodiment, the present invention relates to a process for forming one or more fibers, nanofibers or structures made therefrom on a wide variety of structures or surfaces (e.g., asperities, flat surfaces, angled surface, hierarchical structures, etc.) where such fibers and/or structures are designed to sequester, carry and/or encapsulate one or more substances. In still another embodiment, the present invention relates to structures that contain one or more fiber and/or nanofiber structures on asperities where the nanofiber and/or fiber structures are designed to sequester, carry and/or encapsulate one or more substances.

BACKGROUND OF THE INVENTION

There is an interest in methods to sequester, entrap, encapsulate and/or deposit various compounds or substances on the surfaces of, on various structures, and/or within various structures (e.g., polymer, metal, or ceramic surfaces and/or structures). One area of interest is the use of fibers and/or nanofibers that are designed to carry one or more compounds or substances, where such fibers, nanofibers, or structures made therefrom are placed, deposited or formed on one or more surfaces of a material.

Thus, there is a need in the art for methods, and products, that permit one to include and/or incorporate various fibers and/or nanofibers, where the fibers and/or nanofibers are designed to carry, sequester and/or encapsulate one or more compounds or substances, or are designed to be deposited onto a wide variety of structures and/or surfaces.

SUMMARY OF THE INVENTION

The present invention relates to structures that contain one or more fiber and/or nanofiber structures where such structures can be formed on a wide variety of structures or surfaces (e.g., asperities, flat surfaces, angled surface, hierarchical structures, etc.). In one embodiment, the present invention relates to a process for forming one or more fibers, nanofibers or structures made therefrom on a wide variety of structures or surfaces (e.g., asperities, flat surfaces, angled surface, hierarchical structures, etc.). In another embodiment, the present invention relates to a process for forming one or more fibers, nanofibers or structures made therefrom on a wide variety of structures or surfaces (e.g., asperities, flat surfaces, angled surface, hierarchical structures, etc.) where such fibers and/or structures are designed to sequester, carry and/or encapsulate one or more substances. In still another embodiment, the present invention relates to structures that contain one or more fiber and/or nanofiber structures on asperities where the nanofiber and/or fiber structures are designed to sequester, carry and/or encapsulate one or more substances.

In one embodiment, the present invention relates to a bead-containing asperity comprising: at least one surface having at least one asperity thereon, wherein the at least one asperity is able to collect at least one bead of an electrospun polymer thereby yielding at least one bead-containing asperity, wherein the electrospun polymer contains at least one useful substance therein in an amount sufficient to enable the delivery or use of an effective amount of the at least one substance.

In another embodiment, the present invention relates to a method for preparing a bead-coated asperity, the method comprising the steps of: providing a surface having thereon at least one asperity; forming a liquid polymer jet from the combination of at least one electrospinnable polymer and at least one useful substance, wherein the jet of liquid polymer remains in a liquid or semi-liquid state after being deposited or impinged on the asperity so that the jet forms a droplet that is capable of hardening into at least one bead; and permitting the at least one bead to harden, wherein the electrospinnable polymer contains the at least one useful substance in an amount sufficient to enable the delivery or use of an effective amount of the at least one substance.

In still another embodiment, the present invention relates to a method for producing an electrospun fiber, or nanofiber, structure, the method comprising the steps of: supplying at least one electrospinnable polymer composition to an electrospinning apparatus; spinning at least one fiber, or nanofiber, from the at least one electrospinnable polymer composition; and collecting the at least one fiber, or nanofiber, produced by the electrospinning apparatus on a collector in such a manner as to produce a desired structure.

BRIEF DESCRIPTION OF THE DRAWINGS

FIGS. $24a_1$ through $24c_3$ are optical microscopy mages (see images $24a_1$, $24b_1$, and $24c_1$) and scanning electron microscopy images (see images $24a_2$, $24b_2$, $24c_2$, $24a_3$, $24b_3$, and $24c_3$) of electrospun fibers

FIG. 27 is an image of a continuous electrospun PLLA fiber that buckled in several modes: coiled at the top, zigzag at the bottom and some transitional forms between.

DETAILED DESCRIPTION OF THE INVENTION

Figure 1:
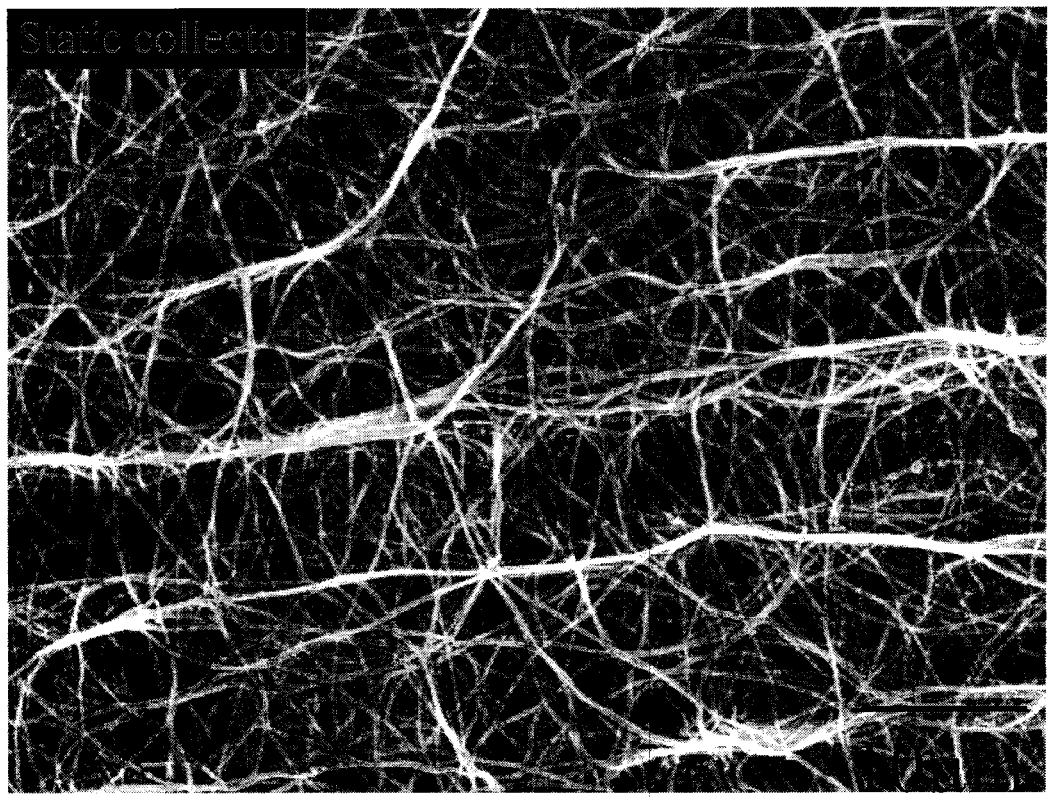
FIGS. 1 through 12 are photographs of various representative fiber and/or nanofiber structures that can be formed via the methods of the present invention.

The present invention relates to structures that contain one or more fiber and/or nanofiber structures where such structures can be formed on a wide variety of structures or surfaces (e.g., asperities, flat surfaces, angled surface, hierarchical structures, etc.). In one embodiment, the present invention relates to a process for forming one or more fibers, nanofibers or structures made therefrom on a wide variety of structures or surfaces (e.g., asperities, flat surfaces, angled surface, hierarchical structures, etc.). In another embodiment, the present invention relates to a process for forming one or more fibers, nanofibers or structures made therefrom on a wide variety of structures or surfaces (e.g., asperities, flat surfaces, angled surface, hierarchical structures, etc.) where such fibers and/or structures are designed to sequester, carry and/or encapsulate one or more substances. In still another embodiment, the present invention relates to structures that contain one or more fiber and/or nanofiber structures on asperities where the nanofiber and/or fiber structures are designed to sequester, carry and/or encapsulate one or more substances.

As used herein the word "asperities" means the "microscopic surface elevations" present on the surface of a material due to surface roughness of a material. Additionally, as used herein nanofibers are fibers having an average diameter in the range of about 1 nanometer to about 25,000 nanometers (25 microns). In another embodiment, the nanofibers of the present invention are fibers having an average diameter in the range of about 1 nanometer to about 10,000 nanometers, or about 1 nanometer to about 5,000 nanometers, or about 3 nanometers to about 3,000 nanometers, or about 7 nanometers to about 1,000 nanometers, or even about 10 nanometers to about 5000 nanometers. In another embodiment, the nanofibers of the present invention are fibers having an average diameter of less than 25,000 nanometers, or less than 10,000 nanometers, or even less than 5,000 nanometers. In still another embodiment, the nanofibers of the present invention are fibers having an average diameter of less than 3,000 nanometers, or less than about 1,000 nanometers, or even less than about 500 nanometers. Additionally, it should be noted that here, as well as elsewhere in the specification and claims, individual range limits may be combined to form additional range limits.

Although not specifically limited to any one production method, the fibers and/or nanofibers of the present invention are, in one embodiment, formed via an electrospinning process. The electrospinning of liquids and/or solutions capable of forming fibers, also known within the fiber forming industry as electrostatic spinning, is well known and has been described in a number of patents as well as in the general literature. The process of electrospinning generally involves the creation of an electrical field at the surface of a liquid. The resulting electrical forces create a jet of liquid that carries electrical charge. Thus, the liquid jets may be attracted to other electrically charged objects at a suitable electrical potential. As the jet of liquid elongates and travels, it will harden and dry. The hardening and drying of the elongated jet of liquid may be caused by cooling of the liquid, i.e., where the liquid is normally a solid at room temperature; evaporation of a solvent, e.g., by dehydration, (physically induced hardening); or by a curing mechanism (chemically induced hardening). The produced fibers are collected on a suitably located, oppositely charged receiver and subsequently removed from it as needed, or directly applied to an oppositely charged or grounded generalized target area.

Fibers produced by this process have been used in a wide variety of applications, and are known, from U.S. Pat. Nos. 4,043,331; 4,878,908; and 6,753,454, all of which are incorporated herein by reference in their entireties. One of the major advantages of electrospun fibers is that very thin fibers can be produced having average diameters, usually on the order of about 1 nanometer to about 25,000 nanometers (25 microns), or about 1 nanometer to about 10,000 nanometers, or about 1 nanometer to about 5,000 nanometers, or about 3 nanometers to about 3,000 nanometers, or about 7 nanometers to about 1,000 nanometers, or even about 10 nanometers to about 500 nanometers. In another embodiment, the nanofibers of the present invention are fibers having an average diameter of less than 25,000 nanometers, or less than 10,000 nanometers, or even less than 5,000 nanometers. In still another embodiment, the nanofibers of the present invention are fibers having an average diameter of less than 3,000 nanometers, or less than about 1,000 nanometers, or even less than about 500 nanometers.

Figure 2:
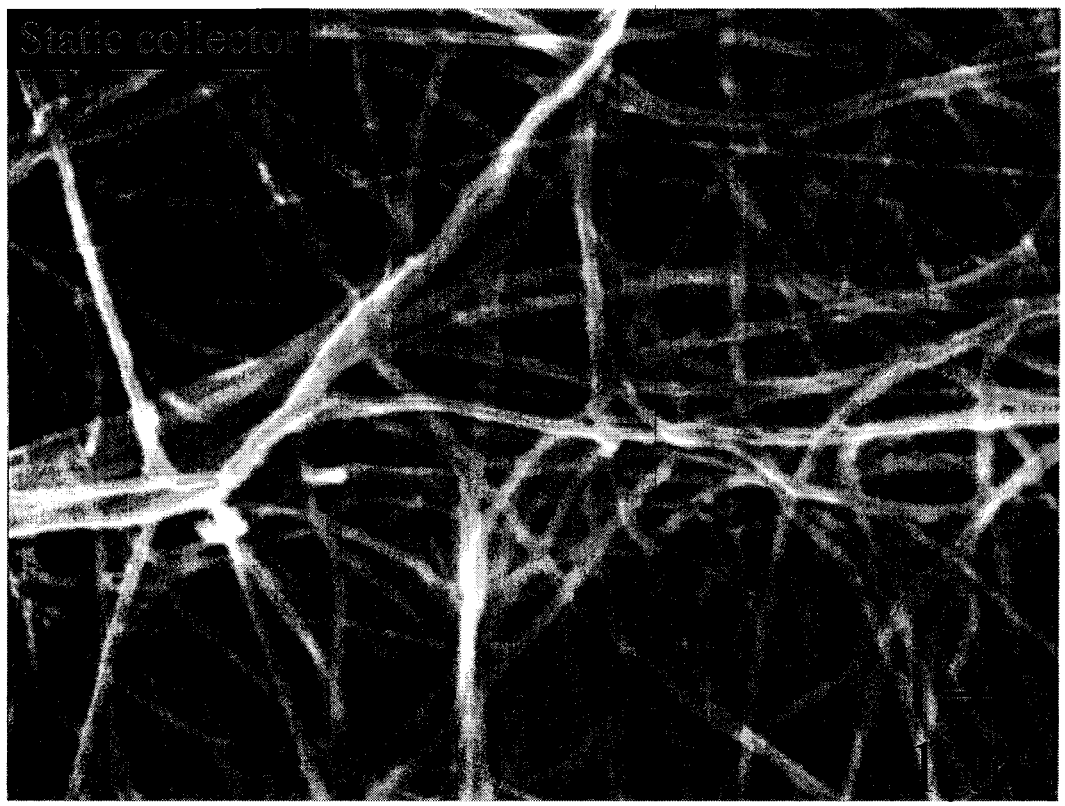
Figure 3:
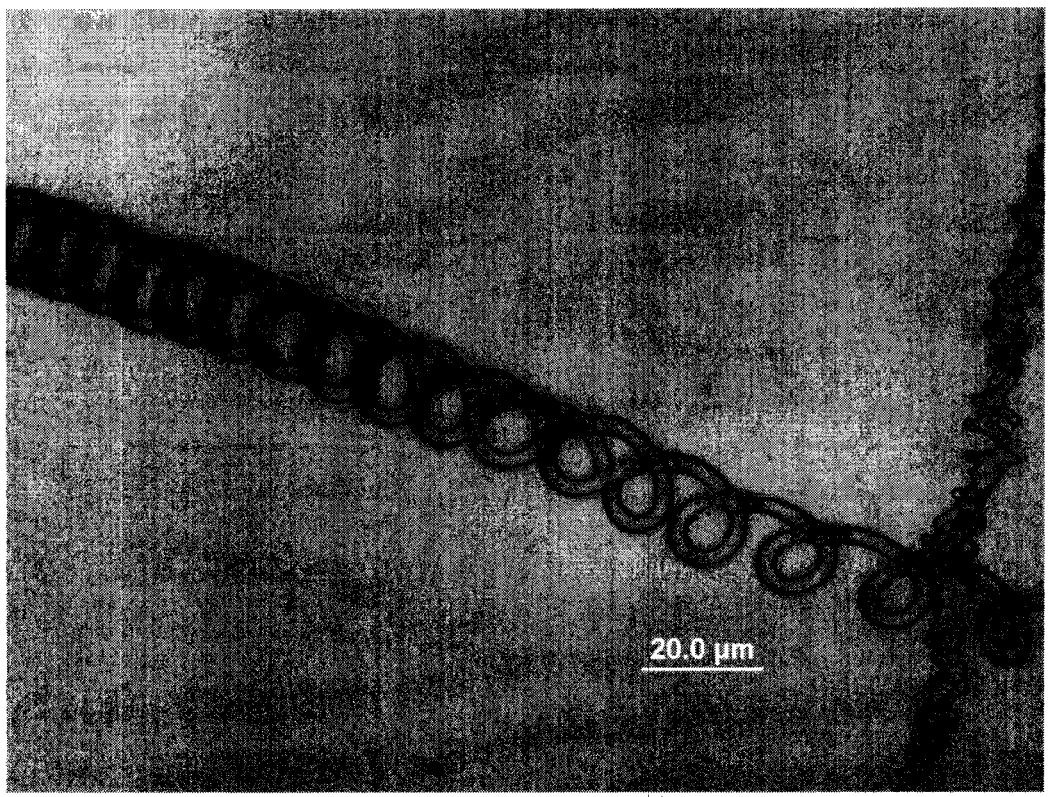
Figure 4:
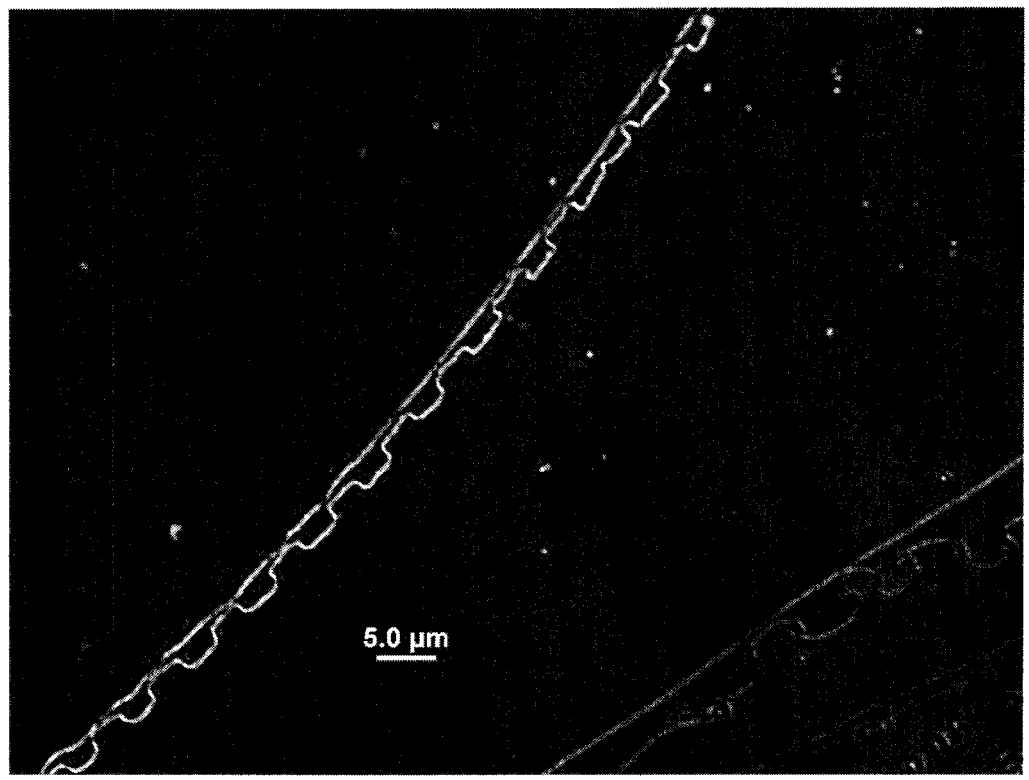
Figure 5:
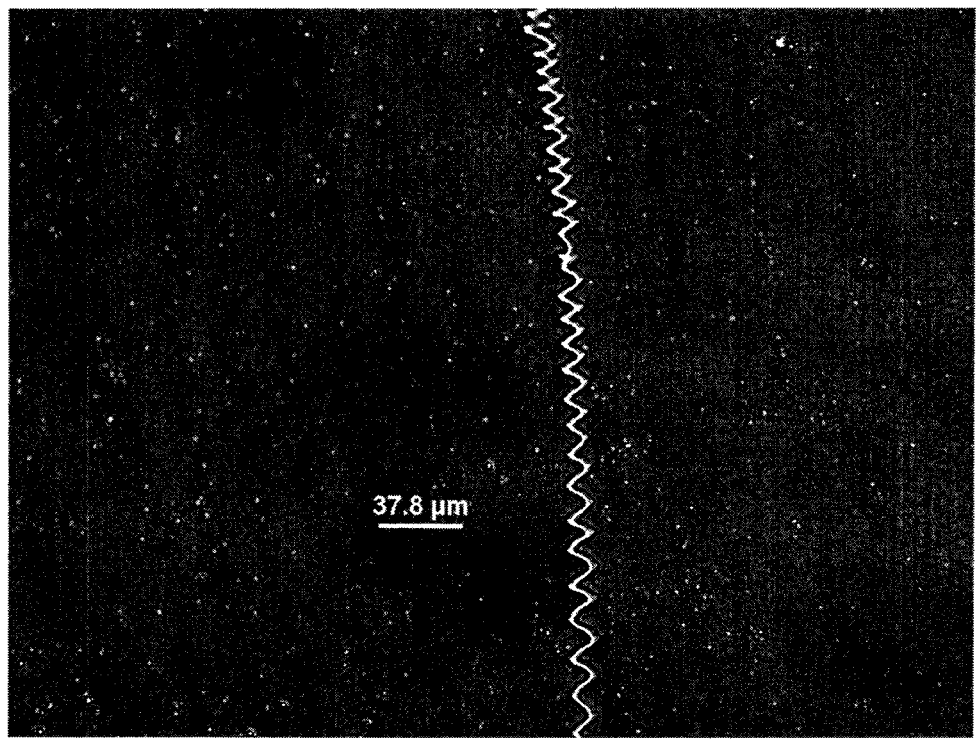
Figure 6:
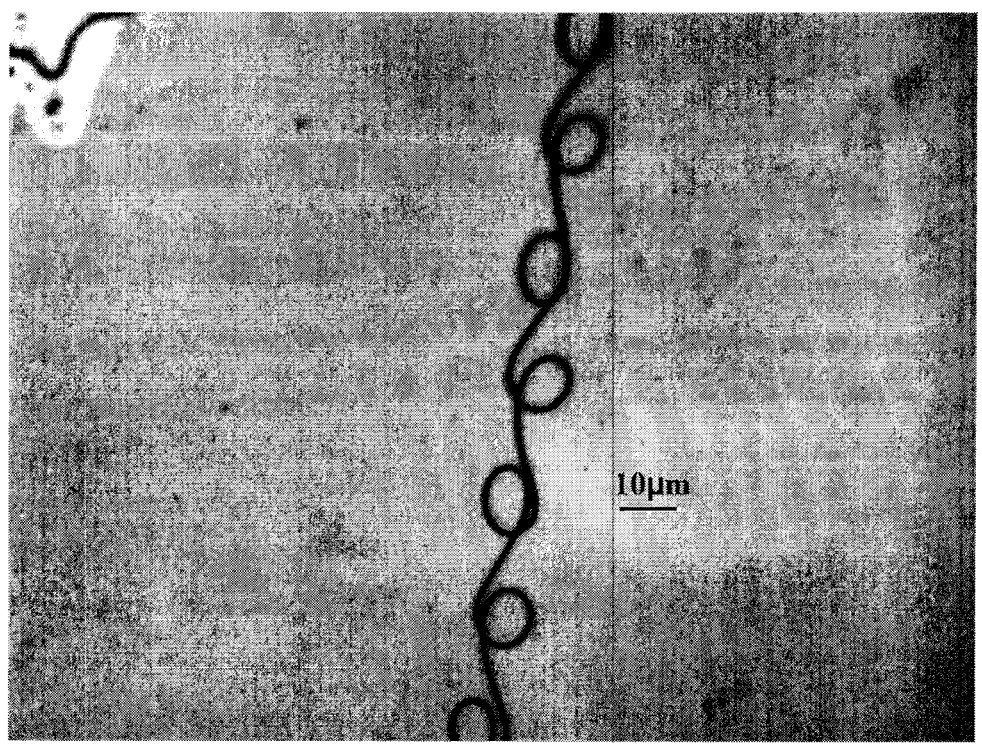
Figure 7:
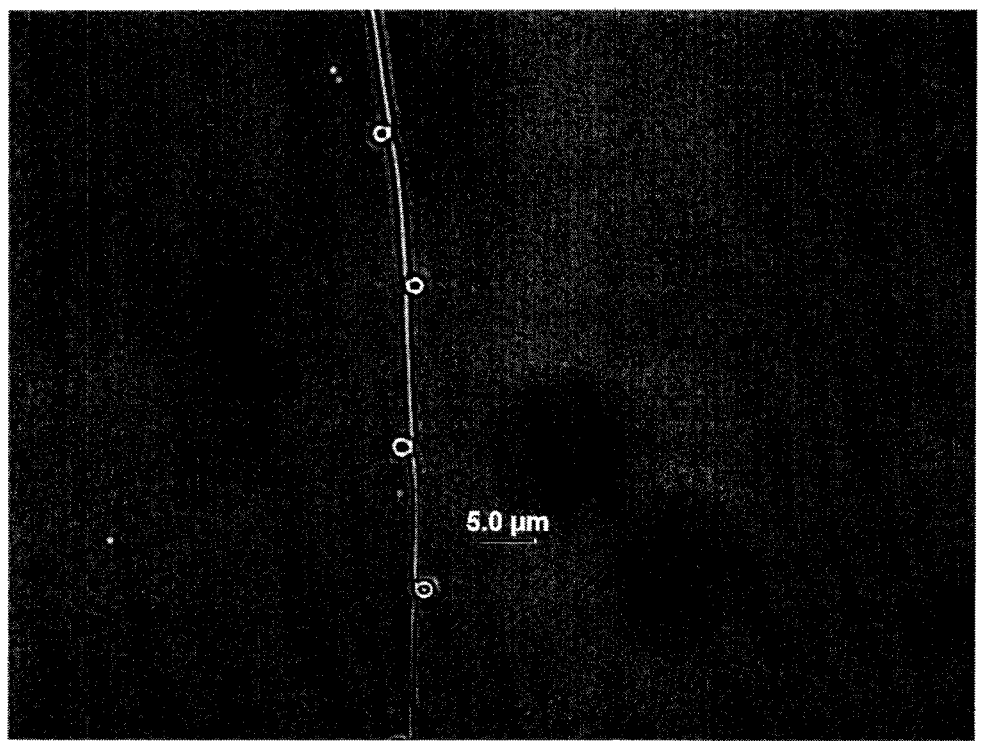

In one embodiment, the present invention relates to methods by which to produce various fiber and/or nanofiber structures. A wide variety of structures, or hierarchical structures, can be produced by the methods of the present invention. Exemplary structures are shown in the photographs of FIGS. 1 though 12. FIG. 1 illustrates a web-like structure formed from one or more fibers and/or nanofibers, with FIG. 2 being a close up of the structure of FIG. 1. FIG. 3 illustrates a repeating loop structure, FIG. 4 a step-like structure, FIG. 5 a zigzag structure, FIG. 6 is a looser loop structure, and FIG. 7 is a wider spaced loop-containing structure.

Figure 8:
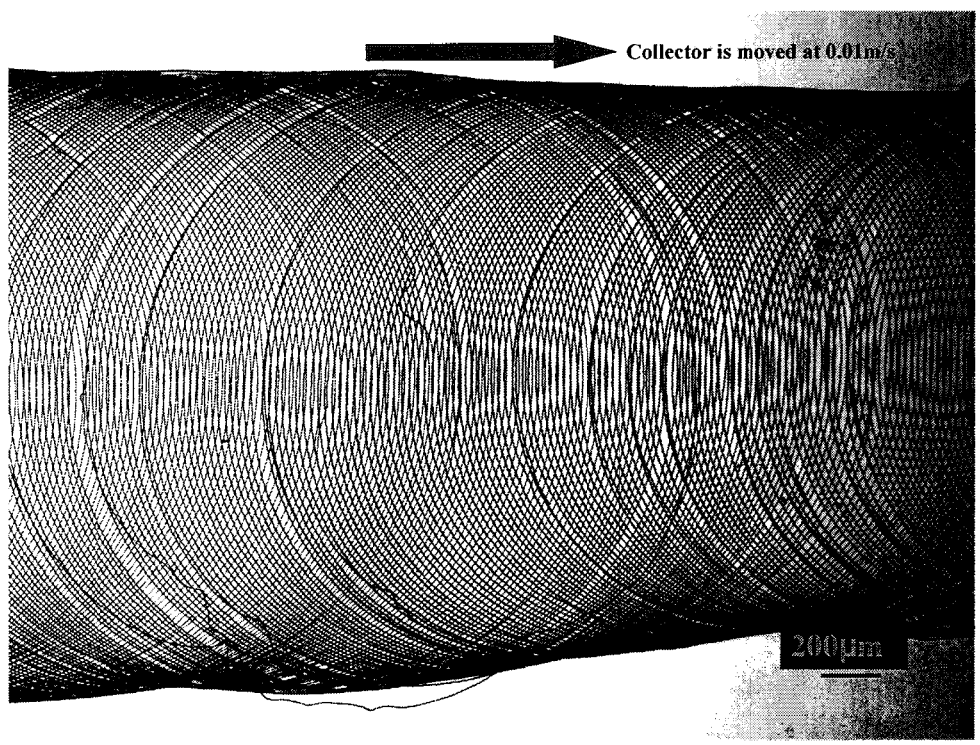
Figure 9:
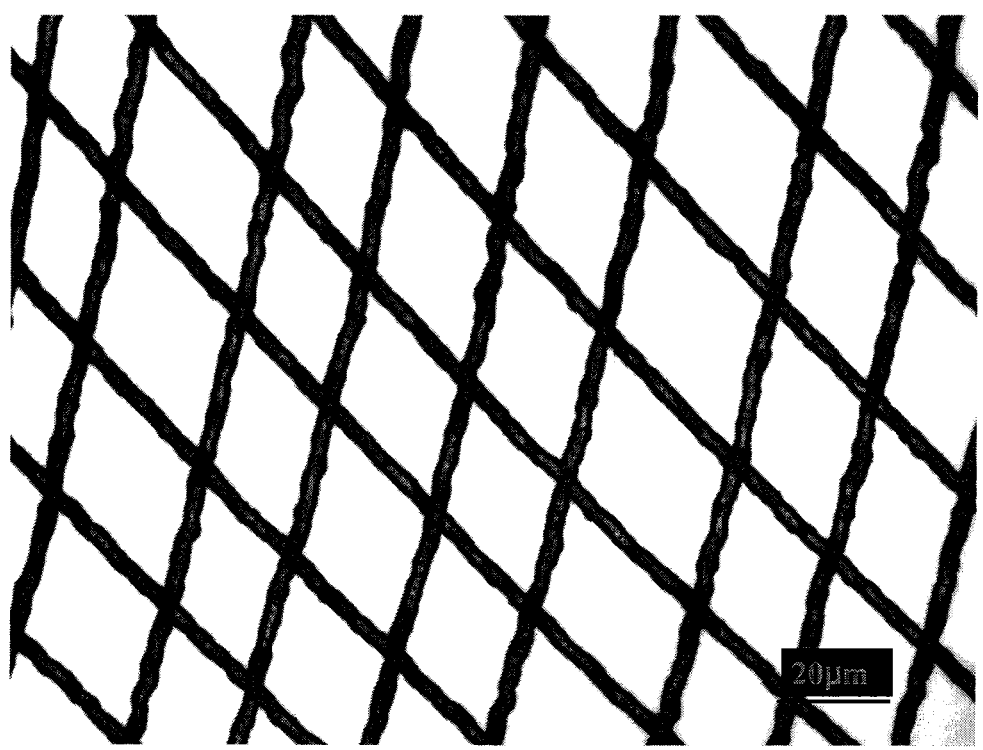

FIGS. 8 and 9 illustrate hierarchical structures which can be achieved via the methods of the present invention. In another embodiment, the structures illustrated in FIGS. 8 and 9 can be used as a base structure to which additional fibers and/or nanofibers can be deposited and/or attached.

Figure 10:
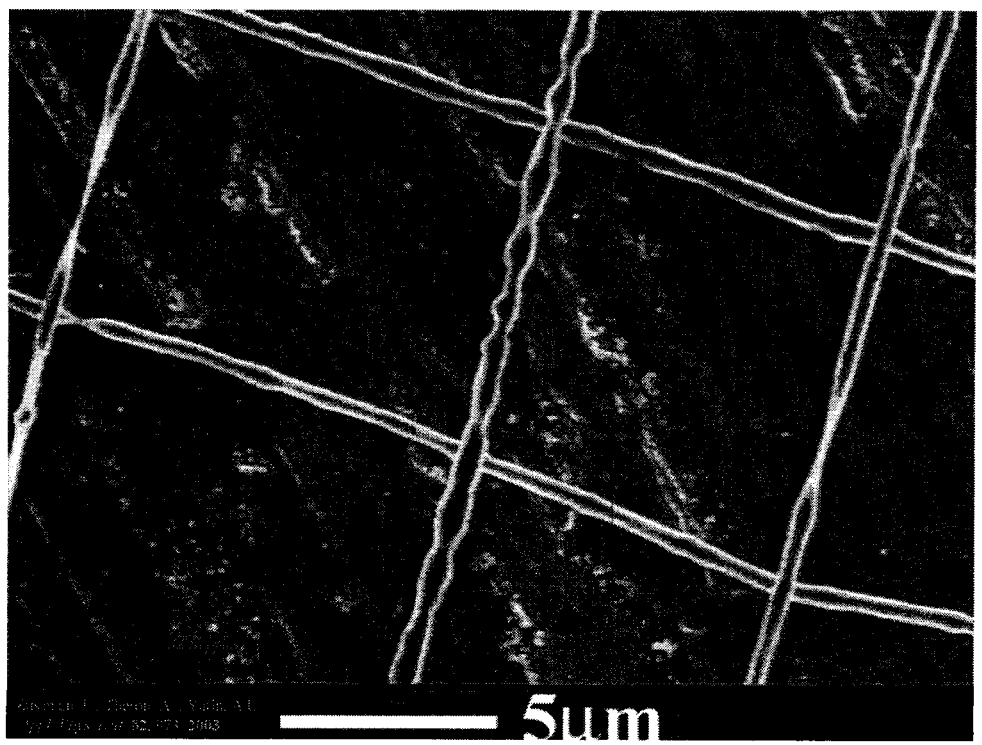
Figure 11:
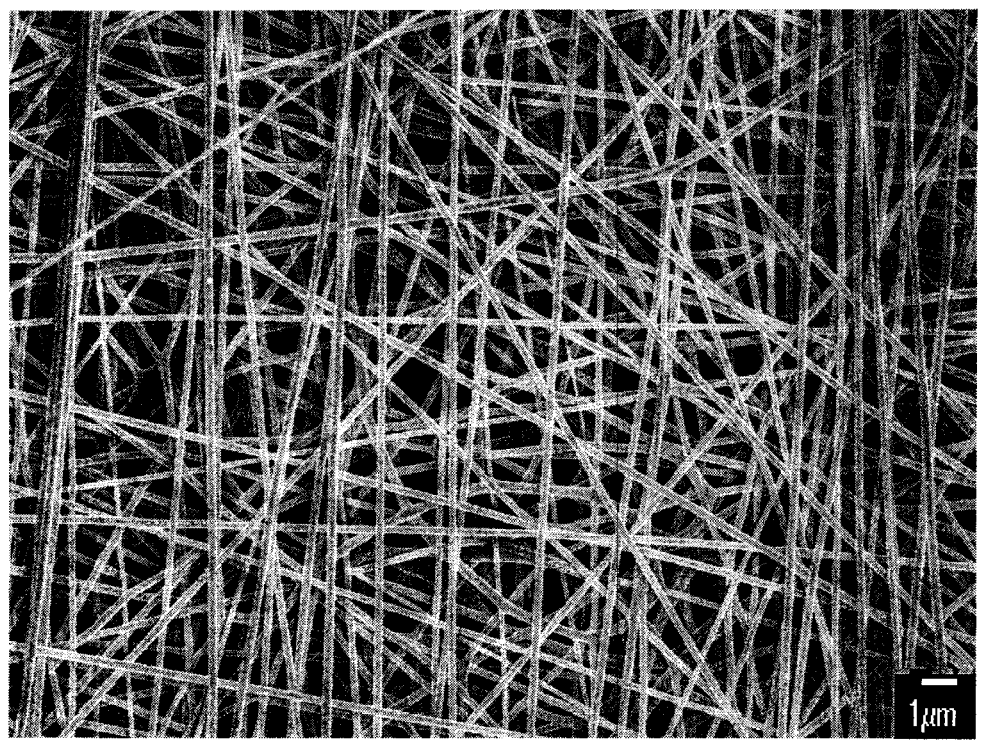
Figure 12:

FIG. 10 illustrates a checkered pattern and FIG. 11 illustrates another web-like structure where the fibers and/or nanofibers of this structure are predominantly straight or nearly straight. FIG. 12 illustrates three different types of structures. The structures of FIG. 12 include a zigzag structure, a repeating star-burst like structure, and a wave-like structure. Although not specifically pictured, other structures are possible such as tube structures, various arrays of loops, coils, and the like.

Given the content of FIGS. 1 through 12, it should be noted that the present invention is not limited to the formation of any one type of structure. Instead, depending upon how the one or more collectors are moved, a virtual infinite variety of fiber and/or nanofiber structures can be formed.

Figure 13:
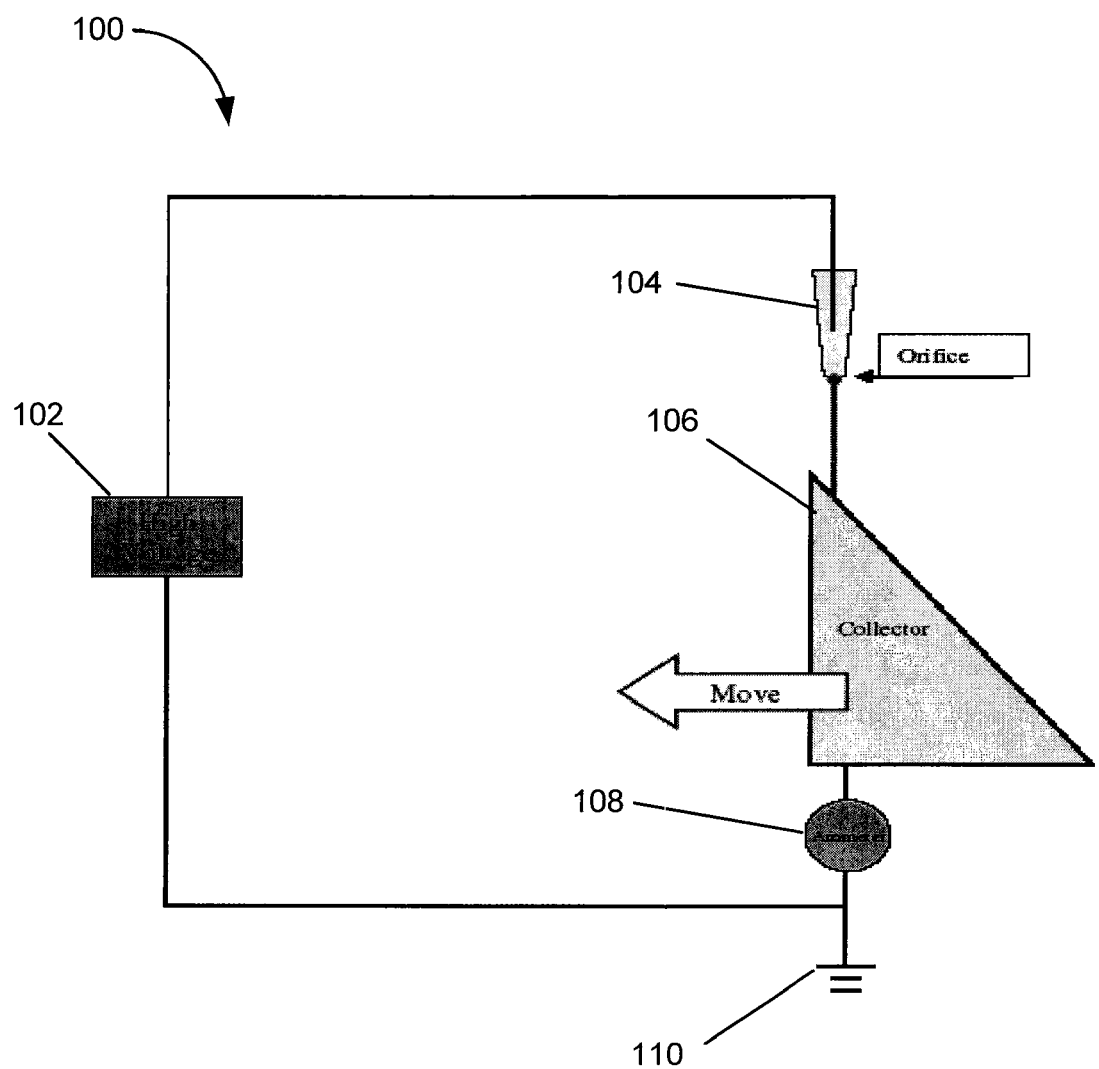
FIG. 13 is a schematic illustration of device for forming fiber and/or nanofiber articles, or products, according to one embodiment of the present invention.

Turning to FIG. 13, FIG. 13 is a schematic illustration of a device designed to produce fiber and/or nanofiber structures in accordance with the present invention. With specific reference to FIG. 13, FIG. 13 illustrates a device 100 designed to produce fiber and/or nanofiber structures in accordance with the present invention. Device 100 comprises a voltage source 102, an electrospinning device 104, a collector 106, an ammeter 108, and a ground 110. Electrospinning device 104 contains therein at least one orifice designed to produce one or more types of fibers and/or nanofibers. As is illustrated in FIG. 13, collector 106 is movable.

It should be noted that although collector 106 is shown as an angled, or slanted, collector, collector 106 is not limited thereto. Instead, any geometrically-shaped collector can be utilized in addition to, or in place of, collector 106. Such possible collector geometries include, but are not limited to, flat surfaces, curved surfaces, undulating surfaces, pyramidal surfaces, surfaces having multiple pyramidal shapes, surfaces formed from multiple semi-spherical shapes, pointed shapes or tips, surfaces having one or more asperities thereon, etc.

It should be noted that any type of material that can be can be electrospun can be used to form fiber and/or nanofiber structures in accordance with the present invention. Such substances include, but are not limited to, polymers, monomers, ceramic precursors, ceramic compositions, metals, metal precursors, carbon precursors (i.e., compositions that yield carbon structures upon further treatment (e.g., upon heating)), or combinations of two or more thereof. In another embodiment, the structures of the present invention can be formed from any material that can be placed into, or suspended in, a solution (e.g., a polymer solution) and subjected to an electrospinning process.

Asperity Embodiments:

Although not limited solely hereto, suitable arrays of asperities can made by the growth of elongated cylindrical crystals by: a vapor liquid solid process; growth of polycyanoacrylate fibers from small deposits of catalyst material; MEMs technology of the sort utilized in the semiconductor electronic industry; removing, by dissolution, fracture, or decomposition, the matrix from a composite that contains acicular particles; and in many other ways known in the art.

As is discussed above, it is possible to incorporate, encapsulate, entrap and/or deposit one or more compounds or substances on, in or around fibers and/or nanofibers. One manner by which this can be accomplished is by dissolving and/or dispersing the desired substance(s) or compound(s) in a polymer solution that is to be electrospun prior to subject such a solution to an electrospinning process. In one embodiment, the material inside the nanofiber is sequestered and preserved by the polymer matrix provided by the nanofiber.

In one embodiment, it is advantageous to coat the asperities with nanofibers which contain useful substances inside or on the nanofiber. Different substances can be concentrated near the tips of the asperities. The high surface area per unit volume of a fiber, in particular a nanofiber, makes it possible to carry a high mass of particles containing bioactive material per unit volume on the outside surface of the fiber and/or nanofiber. In one embodiment, it is even more useful to coat the tips of the asperities with nanofibers carrying one or more useful substances, and to have nanofibers that sequester a second set of useful substances span the regions between the asperities.

If, in one embodiment, the surfaces with asperities are mechanically pressed into contact with a second surface, the nanofibers on top of the asperities will be transferred onto, or impressed into the second surface. If, in one embodiment, the second surface is a sheet of material thinner than the height of the asperities, the nanofibers may be pushed through the sheet and available for chemical reactions or other purposes on the other side of the sheet, while the nanofibers that span the spaces between the asperities are pressed onto the first surface of the sheet.

In one embodiment, the present invention permits a designer to specify the relative amounts and kinds of useful materials, in each of three regions: on the surface near the tip of the asperity, a ball on top of the asperity, and in the space between the asperities. Such designs can be manufactured by one or methods in accordance with the present invention.

In one embodiment, quantities of around 1 microgram of one or more bioactive substances per pin and/or asperities have been found to be useful. For a material with a specific gravity near one, a cube with edges that are 0.1 mm (100 microns) long, would weigh 1 microgram. For nanofibers, the specific gravity is only about 0.2, so the volume required for 1 microgram is correspondingly larger. The edge of a 1 microgram cube of nanofibers is about 170 microns long.

Coatings made of fibers and/or nanofibers for an array of asperities can be designed to produce a variety of useful arrangements of the nanofibers. Thus, in one embodiment, the present invention utilizes an attraction between electrically charged fibers and/or nanofibers and a sharp point. Further, since electrospun nanofibers are very long, the same nanofiber may span the space between adjacent tips and/or be attached to a large number of tips, resulting in the creation of a thin, non-woven sheet supported on the tips of the array of pins.

Other arrangements of the nanofibers, created by the methods of the present invention provide a number of advantages.

In one embodiment, the nanofibers are wrapped around the tip of each asperity to form a relatively thick coating on the tip, with relatively few nanofibers spanning the spaces between the tips. This can be accomplished by controlling the electrospinning process so that the electrospinning jet is collected on the tips held near the location where the onset of the electrically driven bending instability occurs, and further, the jet is nearly dry, but is still soft and can readily bend. These conditions also favor mechanical buckling as the jet is caught and stopped on the tip. Via the present invention, the ability to create such nanofiber structures can be realized.

The combination of these effects, and the presence of the pin, causes the nanofibers to generate a cotton-swab-like ("Q-Tip"-like) collection of nanofibers near the tip of the pin.

Conglutination of the nanofibers can also be controlled, so that the fibers may range from fibers that are not attached to each other an slide past each other at crossing points, or fibers that are mechanically attached to each other at crossing points. The material on which the one or more asperities are formed must be a good enough electrical conductor that charge carried via or on the arriving jet(s) is conducted away. A sufficient level of ionic conductivity exists on the surface of ordinary glass at a normal ambient relative humidity. If a material with an excessively low conductivity is utilized, the effective conductivity of the asperities can be increased sufficiently by coating them with a ten to 1000 nanometer thick layer of carbon or other conductor or conductive material. This can be accomplished by any suitable technique including, but not limited to, vapor deposition, or by evaporation of carbon or metal onto the surface bearing the one or more asperities.

It should be noted that cotton-swab-like shapes can be used as collectors for electrospun nanofibers where, in one embodiment, such collectors are placed on one or more rotating mandrels. In another embodiment, the present invention does not require the use of a rotating pin. Instead, in this embodiment, the arriving nanofiber rotates around the tip region of the pin. This is made to happen locally and separately at the tip of each asperity. When the arriving fiber moves from one asperity to an adjacent one, a nanofiber segment remains between the two asperities, but the total amount of material in the spanning nanofibers is much less than the total amount accumulated near the tips of all the asperities.

In another embodiment, the arriving nanofibers can be accumulated in a "ball" attached to the tip if the electrical conductivity of the collected fibers is kept at a relatively high value as the fiber accumulates. The conductivity of the solidifying nanofibers can be adjusted by addition of ions such as lithium or sodium, and, optionally, with a less volatile liquid substance added to the solvent used in the electrospinning process. The less volatile substance supports ionic conduction of the electrical charge on the arriving nanofiber to the asperity, which is thereby maintained at an attractive electrical potential. This condition allows the arriving nanofiber (which can, in one embodiment, be regarded as a jet solidified enough to retain its fiber-like shape, but still quite soft, sticky, and electrically conducting) to be collected on top of nanofibers that have already been collected. The less volatile solvent can be retained in the collected nanofibers, or in another embodiment this solvent can be evaporated in a time scale a little longer than the time required to collect the desired mass of nanofibers.

In the absence of such ionic conduction through the collected fibers, charge retained on the topmost layer will repel the arriving nanofiber, and cause it to move toward uncoated pins. The uncoated pins may be some distance away; so long lengths of spanning nanofiber can be generated, in the form of a non-woven mat and utilized in some embodiments of the present invention.

Various modes of collection of the one or more fibers, or nanofibers, produced with the present invention are primarily available to a device designer, although the present invention is not limited thereto. On is to cause a fiber, or nanofiber, to be collected on or in front of the tip of the asperity, where the probability of its being pressed mechanically through a thin layer of material is high. Another mode is to form a "non-woven mat" supported on the tips of the asperities. Only a relatively small fraction of the material in such a "non-woven mat" will be carried through the surface as the asperities are pressed against the surface. The remaining matter is brought into intimate contact with the outer surface of a thin layer, where it can be used to protect the surface or in other ways.

In one embodiment, the present invention relates to a structure where the tips of one or more asperities are coated with a cotton-swab-like arrangement of nanofibers bearing one useful material. Another set of useful materials is collected in balls attached to the tip of each asperity. Still another set of useful materials is collected in nanofibers that span the spaces between asperities.

In another embodiment, the present invention relates to multilayer structures where material is collected in the vicinity of the tip of the pin in the "cotton-swab-like" part of the structure, the material collected in "balls" in front of the tip of the asperity, and the "spanning segments" that extend from the tip of one asperity to the tip of an adjacent asperity.

An electrospinning jet that wrapped polyethylene oxide nanofibers around or on the tip of each asperity in an array, is demonstrated by collecting nanofibers on closely spaced carbon fibers of the sort used in reinforced composites, which are electrically conducting, very stiff, and have diameters of about 7 microns. The jet used is, in one embodiment, less than a centimeter in length. Potential differences between the electrospinning tip and the electrically grounded carbon fibers are in the range between about one and about two kilovolts, although the present invention is not limited to just these differences. The diameters of the collected nanofibers are about one micron. The velocity of the jet as it arrived at the tips of the carbon fibers is low, perhaps less than about one meter per second, or perhaps even about one tenth of one meter per second. The specifications above are of a representative experiment and are not intended to act as limitations on the scope of the present invention.

The carbon nanofibers, separated by various distances, are mounted on adhesive tape at lateral distances ranging from about one millimeter to side by side contact. The carbon fibers are projected at different distances toward the jet. Cotton-swab-like coatings are formed on fibers separated by less than one millimeter. Balls are grown on fibers that projected furthest in the direction from which the jet arrives. The balls and cotton-swab-like structures sometimes form at the tips of two carbon fibers which are separated by less than a few tens of microns. A relatively small number of spanning nanofibers extend between fibers that are about one millimeter apart.

Figure 14:
FIG. 14 is a photograph of two 7 micron diameter carbon fibers, one of which has a polyethylene oxide nanofiber bead at the tip and several additional fibers extending down from the tip.

FIG. 14 is a low magnification optical image of 7 micron diameter carbon fibers supported on transparent tape. The divisions in the scale shown in the image are one millimeter apart. The tips of the fibers are coated with polyethylene oxide nanofibers by the electrospinning methods described in this invention. The carbon nanofibers are grounded, and then held about 1 cm below the tip at which the electrospinning jet is created. The orifice from which the jet issued is at the end of a slender glass tube which had an internal diameter of about 60 microns. The potential difference between the electrospinning tip and the carbon nanofibers is about 1.5 kV. The position at which the electrically driven bending instability occurred is noted, and the tips of the carbon fibers are held, by hand, and moving slightly, near this position. The collection of the nanofibers require about 10 or 20 seconds, and are terminated when white spots are visible at the ends of the carbon fibers. The nanofiber coating extends all the way around the tip of each of the carbon fibers.

Figure 15:
FIG. 15 is a wide angle photograph of the same fibers of FIG. 14, plus the surrounding fibers.

FIG. 15 shows a coated carbon fiber tip at higher magnification. The diameter of the coated fiber is about 70 microns, so the radial thickness of the coating is about 30 microns. Several spanning nanofibers can be seen near the tip, showing that the number of spanning nanofibers is smaller than the number of nanofibers on the tip. The end of the coated fiber is rounded. The diameter varies a small amount at different places along the axis. The upper part of the figure is out of focus, and is seen, by focusing on this region, to be smaller in diameter than the region near the tip.

Figure 16:
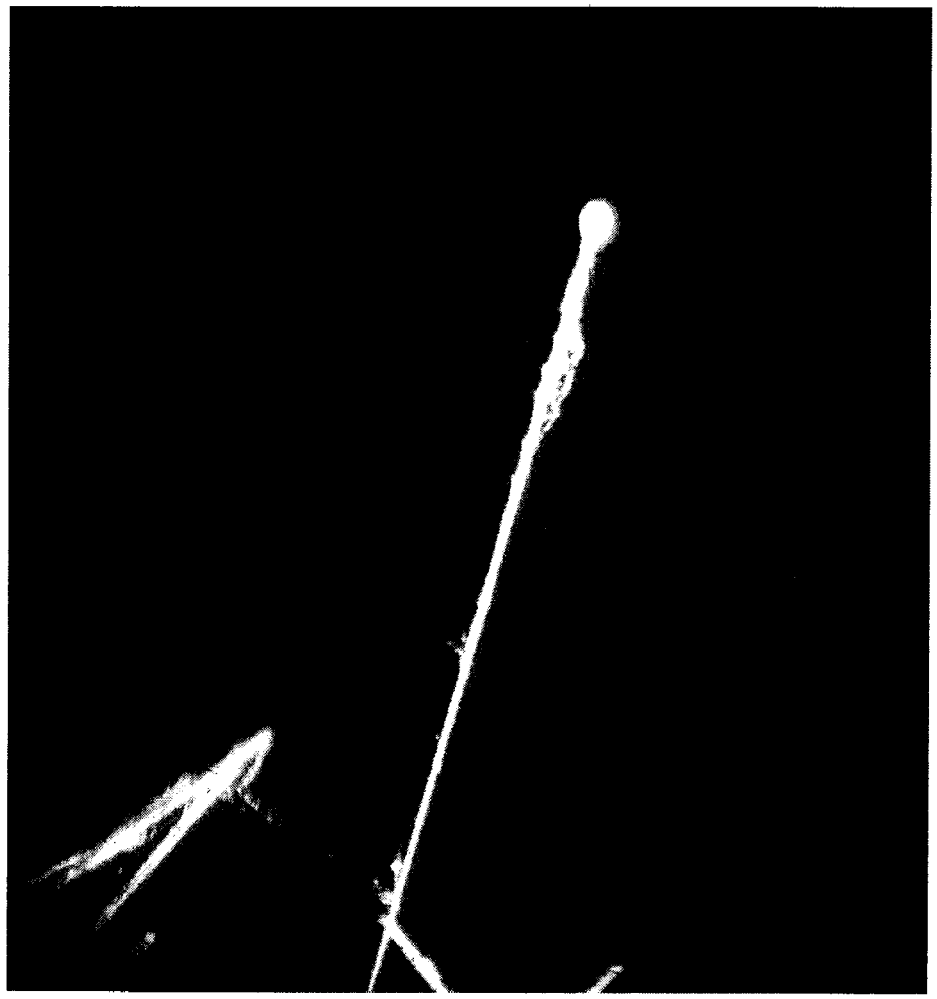
FIG. 16 is a photograph of a 10 mm long jet of fluid impinging on the tip of a 100 micron diameter wire and forming a droplet, which hardens into a bead of polyethylene oxide as the solvent evaporates.

FIG. 16 shows the tip of a carbon fiber, of the same sort as in FIGS. 14 and 15, coated with a ball of nanofibers at the tip. This carbon fiber is extended beyond its neighbors, and is in a position to collect an increased amount of "wetter" fibers in order to create balls on such tip(s) due to the enhanced electrical conductivity of the collected fibers.

If the jet is wet when collected, balls or droplets can also form. The fluid jet carries liquid into the droplet until the charge accumulates to a high enough value to cause the jet to move to a new location, usually leaving a spanning fiber to mark its path. These droplets do not dry as rapidly as nanofibers, but probably still provide significant sequestration and protection to bioactive substances in the fluid. The distinctions between balls of nanofibers and fluid droplets are noted but not emphasized or critical to the present invention.

In one embodiment, structures in accordance with the present invention can be used for ion and fluid transport membranes. Such structures can include, in one embodiment, hierarchical structures formed from multi-walled nanotubes on carbon nanofibers.

The hierarchical structure described includes, in simplest concept, of carbon nanofibers with radial branches which may or may not have metal particles at the end of each radial branch. Each radial branch is electrically connected through a path that is a part of the carbon hierarchical structure, to an external electrical circuit. The methods described in this invention can be used to coat the end of each branch and metal particle with a porous network of polymer nanofibers. If these pores are filled with an ionized network this network can function as a selective ion transport membrane, which is an essential component of a fuel cell. Thus, in one embodiment, the present invention makes it possible to make radical new designs for fuel cells, batteries, and bioelectric contacts. It could also lead to new designs for electrochemical sensors which depend on the motion of ions in the vicinity of an electrode, which is a large class of sensors.

The ability to deposit one kind of nanofiber at the tips of the carbon nanotube branches and other kinds of nanofibers to span the interstices between the tips of the branches makes it feasible to consider new ways of creating essential paths for the flow of gases and liquids through the hierarchical structures of carbon and other materials, including the electrically conducting variations of titanium oxide known as Magnéli phases, and other such conducting or semiconducting materials, some of which could be used to form one or more electrical circuits, or pathways, in a semiconductor chip.

The use of electrospun nanofibers to form durable ion transport membranes is also within the scope of the methods of the present invention. In this embodiment, such membranes could be used in the manufacture of light emitting diodes and photoelectric diodes, where such items are designed to take advantage of the motion of ions in the vicinity of asperities on a surface.

In another embodiment, the present invention can be used to create, produce and/or manufacture devices suitable for injecting one or more bioactive substances through the skin. Given that bioactive substances, (for therapeutic, diagnostic, vaccination, immunization, behavior modification, health monitoring, and other such purposes) need to be injected through the skin, the present invention can aid in this goal by coating the bioactive substance on a tapered pin which is designed to pierce the skin and deposit the bioactive material inside, either as a particle or by dissolving it in blood or other bodily fluids.

In practice it is desirable to use arrays of many pins to achieve efficacious concentrations of the bioactive material inside the body. As used herein, a reference to a pin can mean one or more pins, or pin-like structures, designed to deliver at least one bioreactive substance.

A prototypical pin for this purpose has a diameter of about 100 microns at its broad end and tapers to a sharp tip or chisel edges with somewhat smaller diameter at its other end. The nominal diameter of the tip may, for example, be in the range from about 50 microns to about 5 microns. Such a pin can be inserted through the skin and withdrawn with minimal damage to the skin tissue. However, it should be noted that the present invention is not limited to just the above pin design. Rather, any suitable pin dimensions can be utilized in connection with the present invention.

In one embodiment, it is advantageous to coat the tip of the one or more pins with nanofibers which contain useful substance inside or on the nanofiber. When the coated pin is inserted through the skin, the coating material is distributed between the outer surface of the skin, the surface of the hole created in the skin, and the interior of the body.

In another embodiment, the present invention relates to nanofibers that are carried on a pin that will and/or are designed to absorb substances from inside the body and retain a sample of these substances when the pin is withdrawn. The retained substances can then be analyzed for diagnosis, control, or other purposes. One example of a potential application for a design in accordance with this embodiment, is glucose concentration monitoring.

Nanofibers adhere tightly to the tips and to each other during insertion. When wet with bodily fluids the fibers may become slippery, dissolve, degrade, release bioactive substances by leaching or chemical reaction or produce other useful effects. The material used for the nanofiber and the known possibilities for forming nanofibers from complex mixtures of substances provide many options, which are included in this invention.

The bioactive materials are to be injected through the skin, as described herein. Then spanning nanofibers are applied in a thin layer. For example, the spanning fibers could be a nitric oxide (or chlorine dioxide) releasing structure of the sort described in other co-owned University of Akron patents and/or patent publications. This sort of non-woven mat applied over the top of pins, already coated with the bioactive substances for injection through the skin, could be used both to keep the device sterile between manufacture and use, and to sterilize the skin during and after use. The non-injected material in the spanning nanofibers contributes to an advantageous design that utilizes both injected and non-injected components of the nanofibers.

Since the pins used to carry the nanofibers through the skin are much thicker than the carbon fibers, and in ordered arrays, it is clear from the results obtained with the thin carbon fibers, that microgram quantities of nanofibers can be placed at desired locations, described above, on the arrays of pins created by MEMs fabrication methods.

The cotton-swab-like shape is a desirable arrangement of nanofibers, since the majority of the useful material is attached directly to the part of the pin that will be inside the skin when the device is used.

Reactions between reagents in dry fibers that span the spaces between pins can release a material to disinfect the skin, or to adhere to the skin after the pins are removed and manage fluids escaping from the puncture holes, or for other purposes.

In regard to the asperity examples given above, the following should be noted. In some embodiments, the material on which the one or more asperities are formed should be a good enough electrical conductor to allow charge carried through or on the arriving jet(s) to be conducted away. A sufficient level of ionic conductivity typically exists on the surface of ordinary silicate glass at ambient relative humidity. If a material with an excessively low conductivity is utilized, the effective conductivity of the asperities can be increased sufficiently by coating them with a layer of carbon having a thickness of about 10 to about 1000 nanometers. In another embodiment, the afore-mentioned layer of carbon can be replaces by one or more layers of metal, some other conductive material, or a combination of two or more of the three types of materials described herein.

In another embodiment, the afore-mentioned layer could have a thickness in the range of about 10 to about 100 nanometers, about 100 to about 200 nanometers, about 200 to about 300 nanometers, about 300 to about 400 nanometers, about 400 to about 500 nanometers, about 500 to about 600 nanometers, about 600 to about 700 nanometers, about 700 to about 800 nanometers, about 800 to about 900 nanometers, or even about 900 to about 1000 nanometers. Again, here, as well as elsewhere in the specification and claims, individual range limits may be combined to form additional range limits. The above-mentioned layer, or layers, can be formed by any suitable process including, but not limited to, vapor deposition, or by evaporation of carbon or metal onto the surface bearing the one or more asperities.

In one embodiment, the electrospinnable polymeric compounds of the present invention include, but are not limited to, polyethylene oxide, polyethyleneimine, and polylactic acid, or combinations of two or more thereof.

In some embodiments, it may be advantageous to coat the asperities with beads that contain useful substances inside or on the bead. In this way, a variety of substances can be concentrated near the tips of the asperities. It is possible to incorporate, encapsulate, entrap and/or deposit one or more compounds or substances on, in or around beads. One manner by which this can be accomplished is by dissolving and/or dispersing the desired substance(s) or compound(s) in a polymer solution prior to electrospinning. This permits the modified solution to be converted into a liquid or semi-liquid polymer jet upon application of a suitable electrospinning process. In one embodiment, the material inside the bead is sequestered and preserved by the polymer matrix provided by the bead.

In some embodiments the liquid jet impinges on a plurality of asperities thereby forming a droplet that is supported by the plurality of asperities. Similarly, a droplet can form on a single asperity initially and then grow to the extent that it encompasses one or more nearby asperities. In another embodiment, a liquid jet can split into one or more jets and impinge on a plurality of asperities simultaneously thereby forming a droplet on each asperity.

In some embodiments, a plurality of asperities move relative to a spinneret, thus at least one jet moves from asperity to asperity according to their position. In some variations of this embodiment, the jet leaves one or more fibers as it jumps from asperity to asperity. Thus, a network of beads linked by fibers can be formed.

In another embodiment, the arriving polymer jet can be accumulated in a bead at or about the tip of an asperity if the electrical conductivity of the collected polymer is kept relatively high as the fiber accumulates. The conductivity of the solidifying polymer can be adjusted by addition of ions such as lithium or sodium, and, optionally, with a less volatile liquid substance added to the solvent used in the jet-forming process. In one embodiment, the less volatile substance can support ionic conduction from the polymer jet to the asperity. Thus, in such an embodiment it is possible to maintain the collector, or collecting surface, at an attractive electrical potential due to the above-mentioned conduction. This condition allows the arriving polymer jet to be collected on top of polymer that has already been collected. The less volatile solvent can be retained in the collected polymer, or in another embodiment this solvent can be evaporated in a time scale a little longer than the time required to collect the desired mass of polymer.

In the absence of such ionic conduction through the collected polymer beads, charge retained on the surface repels the arriving polymer jet, and causes it to move toward uncoated pins. The uncoated pins may be some distance away. Therefore, long lengths of spanning nanofiber can be generated. Thus, a network of beads and nanofibers can be formed.

According to some embodiments, useful substances can be dissolved, sequestered or otherwise contained within and/or on a bead. Such substance may be drawn out of the bead upon contact with a suitable solvent, such as water, body fluids, blood, or the like. In one embodiment, one or more useful substances are dissolved in one or more electrospinnable liquid compounds, and beads are formed therefrom that contain the useful substance. According to such embodiments, a polymer solution containing one or more useful substances includes enough solvent to allow an electrostatically formed jet to remain liquid long enough for the jet to impinge on an asperity and form a liquid droplet. The droplet then hardens into a solid bead as the solvent evaporates.

According to some embodiments, the relative amounts and concentrations of useful substances can be predetermined, and/or selected by the practitioner so that sufficient and/or effective amounts of the substance(s) are delivered. In one embodiment, quantities of about 1000 nanograms of one or more useful substances per pin and/or asperities have been found to be useful. For a material with a specific gravity near one, a cube with edges that are about 0.1 mm (100 microns) long, would have a mass of about 1000 nanograms. Other per pin amounts of useful substances include about 1 to about 1000 nanograms, about 1 to about 100 nanograms, about 100 to about 200 nanograms, about 200 to about 300 nanograms, about 300 to about 400 nanograms, about 400 to about 500 nanograms, about 500 to about 600 nanograms, about 600 to about 700 nanograms, about 700 to about 800 nanograms, about 800 to about 900 nanograms, or even about 900 to about 1000 nanograms.

Useful substances within the scope of the present invention include one or more of drugs, pro-drugs, biologics, enzymes, hormones, antigens, vaccines, antibodies, proteins, peptides, amino acids, dyes, fluorescent or phosphorescent compounds, diagnostic agents, therapeutic agents, color-change indicators, and/or adhesives. More specifically, drugs within the scope of the present invention include antibiotics, anesthetics, analgesics, anti-clotting agents, immunosuppressives, statins, birth control, nicotine, antidepressants, anti-anxiety drugs, antipsychotics, psychotropics, and the like. The foregoing substances can be used alone or in any appropriate combination.

If, in one embodiment, surfaces having asperities are mechanically pressed into contact with a second surface, the beads on top of the asperities can be transferred onto, or impressed into the second surface. If, in one embodiment, the second surface is a sheet of material thinner than the height of the asperities, the beads may be pushed through the sheet and available for chemical reactions or other purposes on the other side of the sheet.

Coatings made of beads on an array of asperities can be designed to produce a variety of useful arrangements of the beads. Thus, in one embodiment, the present invention utilizes an attraction between electrically charged beads and a sharp point.

According to some embodiments, a bead can be formed on an asperity, and after it has hardened, another coat of liquid polymer can be deposited onto the bead, thereby forming a layered structure. This can be repeated any number of times, thus creating an unlimited number of layers. Furthermore, each layer can have a different composition and/or contain different amounts of useful substances, or even contain entirely different useful substances.

In other embodiments, nanofibers can be deposited on one or more asperities, and then a liquid polymer jet can be used to coat, cover, and/or encase the nanofibers, thereby forming a layered structure. In such embodiments, the nanofibers and the liquid polymer jet, can have the same, similar, or entirely different compositions, and/or contain any variation of useful substances.

Potential Shapes for the Tips of the MEM Fabricated Pins for the Injection of One or More Bioactive Substances Through the Skin:

Since, in one embodiment, the nanofibers of the present invention are much smaller than the asperities needed to penetrate the skin, the shape of the tips of the pins can be modified to carry more nanofibers through the skin.

Figure 17:
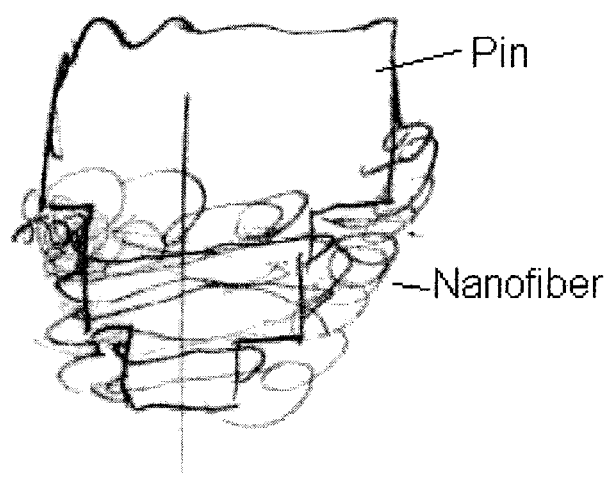
FIG. 17 is a diagram of fibers that are formed on the tip, or point, of a wire, where the wire has steps formed in the end tip thereof.

FIG. 17 is a diagram illustrating a wire with radial steps formed on the end tip thereof, where such steps act to increase the surface area near the tip and provide corners that protect some of the nanofibers from the shearing forces that would otherwise "wipe" the nanofibers off the tip as it is forced through the skin.

Figure 18:
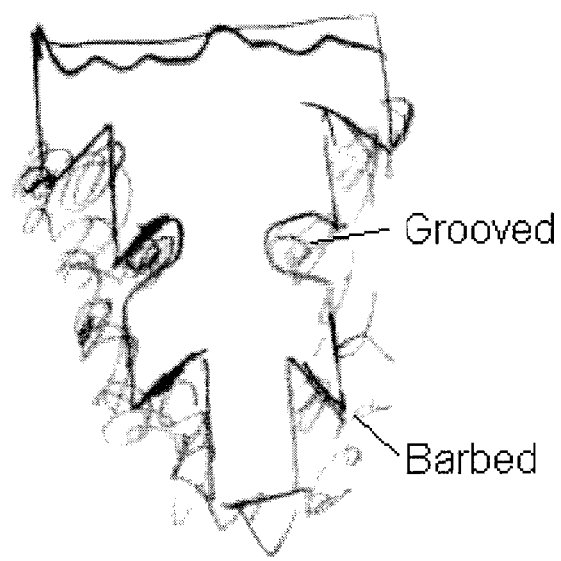
FIG. 18 is a diagram of fibers that are formed on the tip, or point, of a wire, where the wire has a combination of grooves and barbs formed in the end tip thereof.

FIG. 18 provides even more protection of against wiping off of material to be injected, obtained by the creation of a combination of grooves and forward facing barbs and also illustrates the use of circumferential grooves to protect the fibers from wiping.

Figure 19:
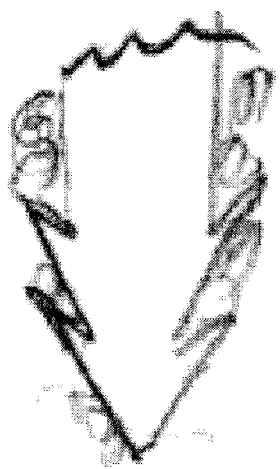
FIG. 19 is a diagram of fibers that are formed on the tip, or point, of a wire, where the wire has multiple barbs formed in the end tip thereof.

FIG. 19 is a diagram illustrating a wire tip that has backward facing barbs formed therein so as to protect some of the nanofibers from wiping as the point is inserted, and also tend to carry some of the nanofibers as the tip is withdrawn. The withdrawn material would then be available for analysis. Only the region close to the tip of the pin is shown in these three figures. The patterns shown are not limiting. These patterns may continue in the same way or with variations along the entire surface of the pin.

Other Applications for Spatially Controlled Deposition of Electrospun Fibers:

Appropriate nanofibers could be applied to the edge of a blade, such as a razor blade, or on or between multiple blades or to the piercing edges of a syringe needle. The fibers could aid in the lubrication, prevent corrosion, or minimize bleeding for example.

The needle could be coated with the fibers. These fibers may be adjuvant polymers, such as PVP. Upon injection of the vaccine, the adjuvant, polymer fibers provide lubrication during insertion. The same or another kind of fiber can also serve as an adjuvant.

Multiple layers of fibers or composites that have varied chemistries, like the NO delivering patches, with vitamin C spun out on one pin and nitrite spun out on another, or fibers containing each are spun onto the same needle. The fibers deliver the NO when moisture from the skin, or from a puncture of the skin activates the reagents. For some applications the reagents may be placed on the separate pins which are inserted at the same time.

The spinning methods utilized in the present invention can also be used to coat only the surface of a stent, without forming a web between the struts of a stent. Only the metal is coated; thus we are not making a stent graft but a fibrous coating that allows fluids to flow through the open interstices of the stent during insertion, and fluids can have direct access to the interior surface of the blood vessel through these interstices after the stent is inserted.

The maneuverable (directable) nature of the jets used in this invention can improve application of fibers skin. Fine details of the wound can be coated with less "bridging" than when a typical bending and coiling jet is used. Before when one tried to spin fibers, or nanofiber, structures in an attempt to control a bleeding wound (e.g., fibers spun onto a liver wound on a dog), the fibers tended to tent over the wound surface. Now one may be able to deliver fibers directly to a specific surface, say a grounded surface on a wound. This can enable the selective delivery of, for example, a polymer containing a small quantity of growth factor to enhance healing of a wound, or certain portions thereof. This may be useful in plastic surgery, where only a small incision needs to be treated this way. A small wire may be laid on top of the incision, and function as the target or ground, that provides even greater control of the place at which the fiber is attached to the wound.

Controlled jets of the sort described in this invention can be used in laparoscopic surgery to cover, protect, medicate, mechanically stabilize or treat tissues to which a surgeon has only very limited access.

Other Fiber and/or Nanofiber Structures:

As is noted above, the present invention is not limited to just the formation of asperity structures. Rather, a wide range of fiber and/or nanofiber structures can be formed in accordance with the present invention.

In one instance, the determination of the behavior of the jet path in the vicinity of the onset of the primary electrical bending instability is important for the orderly collection of the nanofibers produced by electrospinning. A stable jet can be observed with a high frame rate, short exposure time video camera. Given the present invention, the collection process enable thereby can be predictable and reproducible. Thus, the design and creation of a wide variety of two or three dimensional structures of nanofibers is feasible.

In one embodiment, the fluid jet in the straight segment of the path, and the more solid nanofibers in the coils of the primary electrical bending instability are collected on stationary and moving surfaces. The diameter and characteristic path of the jet depended, in one embodiment, on the exact distance between the orifice and the collector, if the other electrospinning parameters are not changed. The moving collector surface causes the various coils that are collected to be displaced rather than superimposed. The fiber, or fibers, collected on the moving surface preserve a record of the electrical and mechanical instabilities that occur. If the straight segment is very fluid, the jet forms a series of small sessile drops on the collector, but when the jet is more solid, buckling occurs and produces small, complicated loops close to point at which the jet hit the surface. Buckling is observed during collection of the straight segment and the first coils of the electrically driven electrical bending instability. A moving inclined collector is used to collect the fibers. Surface velocities are up to about 5 meters per second. However, the present invention is not limited to any one set of collection velocities. Rather, any suitable velocity can be utilized in connection with the present invention.

In one embodiment, the velocities utilized are commensurate with the velocities at which the solidifying jet approaches the collector surface. A variety of structures of loops, both conglutinated and not, associated with the instabilities are created.

The jets used in the following examples are formed from solutions of polyethylene oxide, nylon-6, poly lactic acid, and other polymers. However, as is noted above, the present invention is not limited to just polymeric compounds. Rather, any compound, or mixture of compounds, that can be electrospun can be utilized herein. In the case of the above-mentioned polymers, several solvents are used for some of the polymers, and details of the jet path changed when the solvent or the concentration of solvent changed. The jets issued from a pendent drop on a glass capillary with an orifice diameter of about 160 microns. A potential difference in the range of 500 to 13,000 volts is applied between the orifice and the collector (see FIG. 13). The distance from the orifice to the grounded collector is varied from 1 mm to 30 cm. Interference colors associated with jet diameters around 10 microns are observed in the straight segment. The color patterns are stable, indicating that the process variations are small.

EXAMPLES

Polyethylene oxide (PEO), $M_w$=400,000 g/mol, 6 wt % solution in distilled water; Poly (L-lactide) (PLLA), $M_w$=152,000 g/mol, are dissolved in hexafluoroisopropanol (HFIP) to make a 5% solution; nylon-6, 10% solution in HFIP/Formic acid (FA) mixture, HFIP:Formic acid=8:2 (weight ratio). All chemicals used in these experiments are obtained from Sigma-Aldrich. A JEOL 5310 scanning electron microscope and Olympus 51BX optical microscope are used to characterize the electrospun fibers. A flash camera and a high speed camera that recorded up to 2000 images per second are used to record the morphology of the jet path. The polymer solutions are held in a glass pipette which had a 2 cm long capillary at one end. The capillary's inner diameter is 160 µm. A copper wire is immersed in the solution and connected with an adjustable high voltage power supply. A grounded plate is placed from 1 mm to 300 mm below the orifice. The collector can be moved laterally at speeds of 0 m/s to about 5 m/s. The distance between the orifice and the collector is adjusted from about 1 mm to about 100 mm. The jet path followed the curved electric field lines, so that the actual length of the path is little longer than the perpendicular distance between the plate and the orifice.

In one instance, the appearance of the collected fibers is not greatly changed by the inclination. An ammeter is connected between the collector and grounded wire to measure the current carried by the electrospinning jet. In another embodiment, the ammeter can be eliminated. The collected fibers are observed with optical microscopy and scanning electron microscopy.

Figure 20:
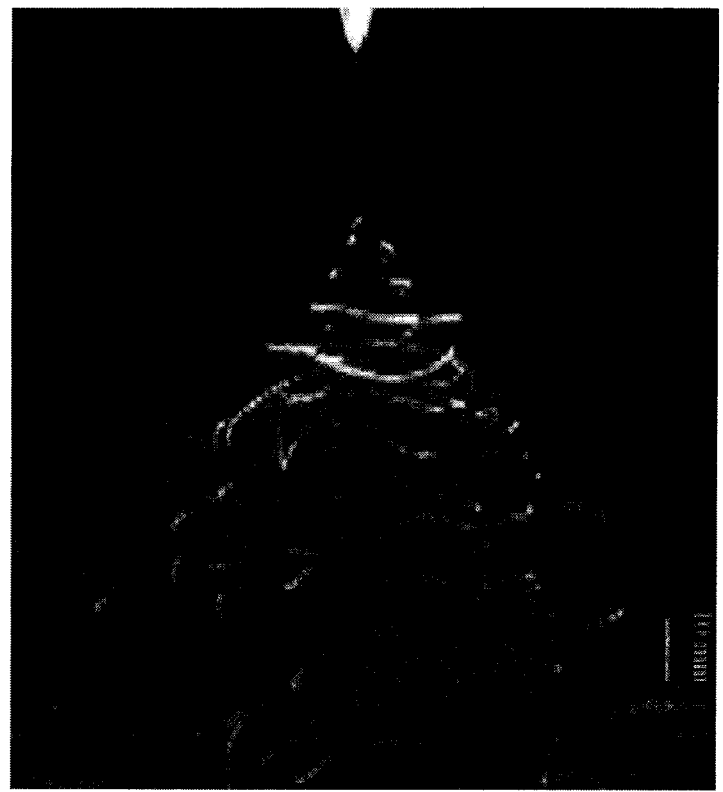
FIG. 20 is a photograph of an image of the instantaneous path of an eletctrospinning jet with well developed coils created after the onset of the electrical bending instability.
Figure 21:
FIG. 21 is a photograph of a straight electrospinning jet.

The electrospinning jet flows continuously from the surface of the drop when the applied electrical force overcame the surface tension. The jet moves straight away from the orifice for some distance and then becomes unstable and bends into coiled loops (FIG. 20). When the distance between the orifice and grounded collector is reduced to less than the length of the maximal straight segment observed with the collector far from the orifice, the electrical bending instability does not occur and only a straight jet is produced (FIG. 21). In this case, it is possible, if so desired to collect straight fibers, or nanofibers. Accordingly, depending upon the movement of the collector surface, it is possible to form grid-like structures, or other straight-lined patterns, with the present invention.

Electrical Bending Instability as a Function of Distance From the Orifice

The onset of the electrical bending instability is investigated by continuously increasing the distance from the orifice to the collector. An inclined grounded collector is placed beneath the electrospinning spinneret (FIG. 13). The perpendicular distance from the orifice to the collector is set at 1 mm and then the inclined collector is moved laterally. PEO in an aqueous solution is used. The distance between the orifice and the collector surface is continuously increased to 75 mm as the inclined collector moves. The voltage between the spinneret and the collector is 5.4 KV.

Figure 22:
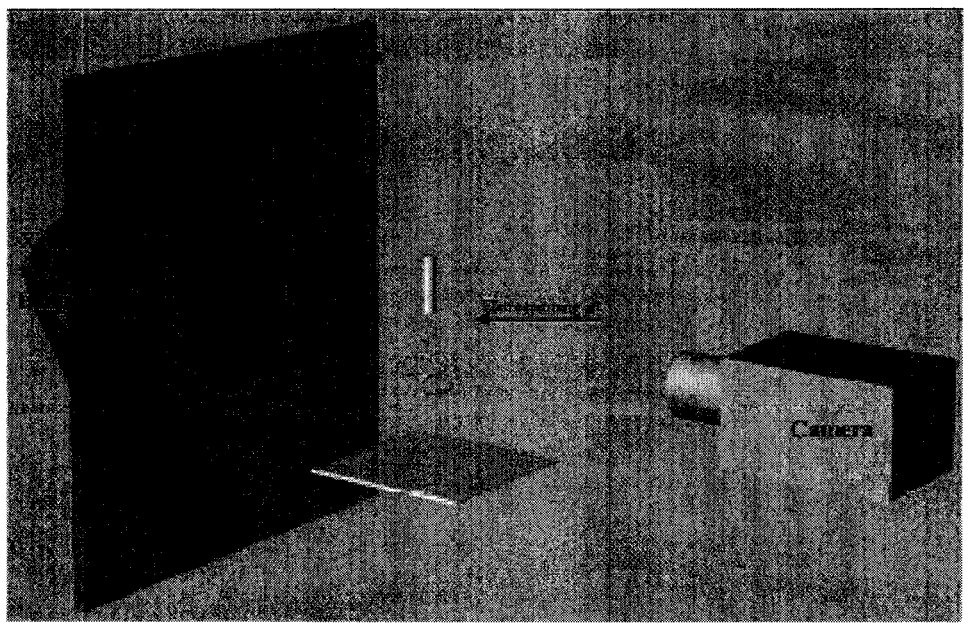
FIG. 22 is a schematic of a camera setup for the observation of an electrospinning jet in accordance with the present invention.

A flash camera and a high speed camera are used to record the morphology of the jet path (FIG. 22). The Fresnel lens produces a converging cone of white light at the location of the electrospinning jet. The opaque disk on the Fresnel lens prevents light from the Xenon arc lamp from entering the camera, but enough light is scattered by the jet, enters the camera and enables the recordation of the path of the jet.

Turning to FIGS. 23a through 23f, this series of photographic images represent the behavior of an electrospinning jet given the variation of certain process parameters. With regard to FIGS. 23a through 23c, these images are from video camera (60 frames/second) images of an electrospinning jet at different collector parameters, while FIGS. 23e through 23g are high speed camera images (2000 frames/second; shutter speed 1/10,000) of the electrospinning jet. The distances from the orifice to the grounded collector (H) increases from left to right. For FIGS. 23a and 23e, H=25 mm; for FIGS. 23b and 23f, H=53 mm; and for FIGS. 23c and 23g, H=75 mm. It should be noted that the present invention is not limited to any one set, or range, of collector heights H. Rather, any desired collector height H can be used in conjunction with the present invention. With regard to FIGS. 23a through 23g, the edge of the collector can be seen in the images as a broad white inclined line.

Figure 23:
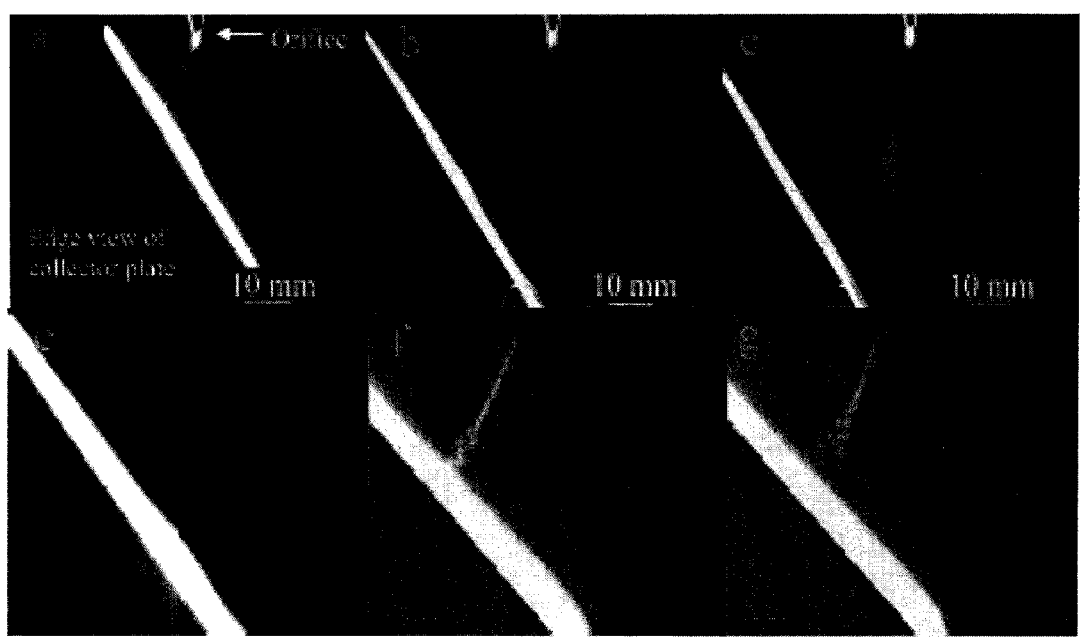
FIGS. 23a, 23b and 23c are a series of photographs (60 frames/second) illustrating an electrospinning jet at different collector parameters.
FIGS. 23e, 23f and 23g are a series of high speed camera images (2000 frames/second; shutter speed 1/10,000) of an electrospinning jet.

Additionally, FIG. 23 shows time averaged (see images a, b, and c) and instantaneous (see images e, f, and g) paths of the electrospinning jet at different distance between the orifice and the collector. When the jet leaves the orifice, it moves to the collector and produces a straight jet. No electrical bending instability is observed when the orifice to collector distance is short. Both the digital camera image (FIG. 23a) and the high speed camera image (FIG. 23e) show an essentially straight jet. When the distance is increased to 53 mm, the digital camera shows a blurred image (FIG. 23b) of the jet and the high speed camera image (FIG. 23f) shows that electrical bending instability has indeed occurred. The coiled loops grow in radius and propagated along a slightly curved electrical field line as they move downward at a speed of about 2 m/s to about 5 m/s.

Figure 24:
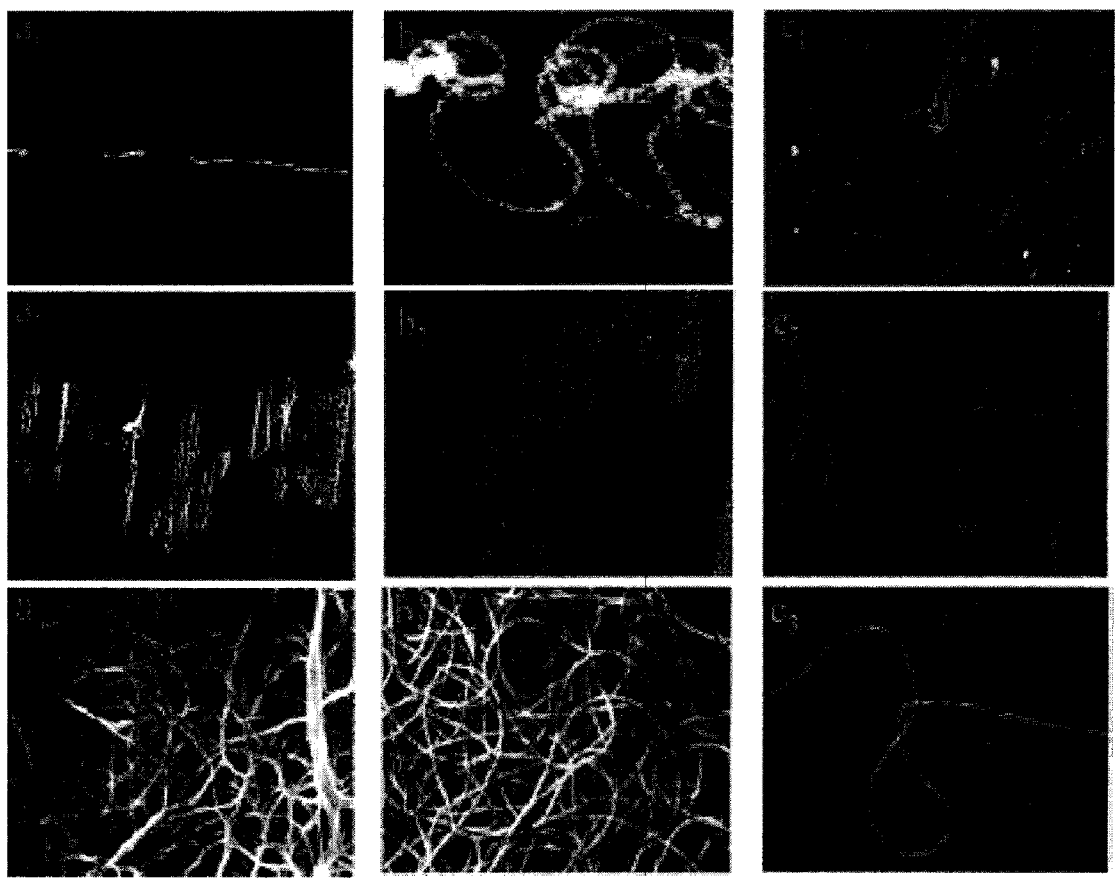

With increasing collection distance, the digital camera (FIG. 23c) shows interference colors indicating that the jet has a diameter of more than about 10 micrometers at the top and about 2 micrometers at the onset of the electrical bending instability; the high speed camera (FIG. 23g) shows the coiled loops of the electrical bending instability. Before the electrical bending instability, the path curves so that the jet approached the plane of the collector in a more nearly perpendicular direction. In each repetition of this experiment, one single trace of the electrospun fiber is collected on the laterally moving collector. The optical and scanning electron microscopy images (FIG. $24a_1$ to FIG. $24c_2$) show the changes in the collected fibers as the orifice to collector distance increases. The straight electrospinning jet produces conglutinated fibers and buckled fibers (FIG. $24a_1$). These fiber segments had a wide diameter distribution that ranged from about 300 nm to about 1 µm (FIG. $24a_2$). After the start of an electrical bending instability, the jet produced loops (FIG. $24b_1$) with diameters ranging from about 50 to about 200 µm. FIGS. $24b_2$ and $24b_3$ show short segments of the electrical bending instability coils in FIG. $24b_1$ at a higher magnification. The amount of conglutination is smaller than that shown in FIGS. $24a_2$ and $24a_3$. The segments of fibers in FIG. $24c_1$ are collected after the primary electrical bending instability loops are much larger than the area shown. The segments shown are only slightly curved. Some segments have nearly periodic curved shapes and small loops that are characteristic of buckling. FIG. $24c_3$ show an enlarged image of a loop made by buckling. With regard to the images in FIG. 24, the following should be noted. The optical microscopy images ($24a_1$, $24b_1$, and $24c_1$) and scanning electron microscopy images ($24a_2$, $24b_2$, $24c_2$, $24a_3$, $24b_3$, and $24c_3$) of electrospun fibers. The length of the horizontal edges of the optical microscopy images ($24a_1$, $24b_1$, and $24c_1$) are about 450 μm; the length of the horizontal edges of the SEM images are 65 μm ($24a_2$, $24b_2$, and $24c_2$) and 13 μm ($24a_3$, $24b_3$, and $24c_3$). The distance from the orifice to the collector is about 25 mm in ($24a_1$, $24a_2$, and $24a_3$), 53 mm in ($24b_1$, $24b_2$, and $24b_3$) and 75 mm in ($24c_1$, $24c_2$, and $24c_3$). Table 1 below details the data associated with the images of FIG. 24.

Buckling Instability of Electrospinning Jet:

In one embodiment, the buckling of a viscous jet can be attributed to the fact that a viscous jet may be either in tension or compression, depending on the velocity gradient along its axis. When axial compressive stresses along the jet reach a sufficient value, the fluid mechanics analogue to the buckling of a slender solid column occurs. In the electrospinning process, the buckling instability occurs just above the collector where the electrospinning jet is in compression as it encountered the collector surface.

The Reynolds number and the distance, between the orifice and the flat collector, called the fall height are two parameters

TABLE 1

| Instability Mode | FIG. | Solution Polymer | Solvent | c % | Wavelength μm/cycle | Frequency cycles/sec | Length of Fiber in μm/cycle | Wave Number cycle/min |
|---|---|---|---|---|---|---|---|---|
| Electrical | 20 | PEO | Water | 6 | | | | |
| Bending Coils | 23b, 23c, 23f, and 23g | PEO | Water | 6 | | | | |
| | $24b_1$ and $24b_2$ | PEO | Water | 6 | 48~200 | $0.5 \times 10^3$~$2.1 \times 10^3$ | 150~628 | 5~21 |
| | $24c_1$ | PEO | Water | 6 | | Buckling on Bending Loops | | |
| | 25 | PEO | Water | 6 | | | | |
| | 28b | Nylon 6 | HFIP/FA | 10 | 29 | $3.45 \times 10^3$ | 578 | 57 |
| | 28c | Nylon 6 | HFIP/FA | 10 | | Superimposed Bending and Buckling | | |
| | 28d | Nylon 6 | HFIP/FA | 10 | 55.3 | $1.81 \times 10^3$ | 2101 | 18.1 |
| | 28e | Nylon 6 | HFIP/FA | 10 | 55 | $1.82 \times 10^3$ | 4741 | 18.2 |
| Mechanical Buckling, Coils and Folds | $24a_2$, $24a_3$, $24b_2$, $24b_3$, $24c_1$, $24c_2$, and $24c_3$ | PEO | Water | 6 | | | | |
| | 26a | PLLA | HFIP | 5 | 11.7 | $0.86 \times 10^4$ | 30 | 85.5 |
| | 26b | PLLA | HFIP | 5 | 6.4 | $1.56 \times 10^4$ | 81.6 | 156 |
| | 26c | PLLA | HFIP | 5 | | Pit of Plane Buckling by Folding | | |
| | 26d | PLLA | HFIP | 5 | 6.4 | $1.56 \times 10^4$ | 60 | 156 |
| | 27 | PLLA | HFIP | 5 | | Transition Buckling Modes | | |
| | 28a | Nylon 6 | HFIP/FA | 10 | | | | |
| | 28b | Nylon 6 | HFIP/FA | 10 | 2.6 | $7.57 \times 10^5$ | 31.4 | 385 |
| | 28c | Nylon 6 | HFIP/FA | 10 | | Superimposed Bending and Buckling | | |
| | 28d | Nylon 6 | HFIP/FA | 10 | 8.5 | $4.47 \times 10^5$ | 34.7 | 118 |
| | 28e | Nylon 6 | HFIP/FA | 10 | 20.18 | $4.26 \times 10^5$ | 44.8 | 49.6 |

Velocity of the collector is 0.1 m/s.

Onset of an Electrical Bending Instability in the Straight Segment:

The PEO aqueous solution held in the pipette is connected to the power supply. The distance from the orifice to the collector is 53 mm. The high frame rate camera is used to observe the jet path.

Figure 25:
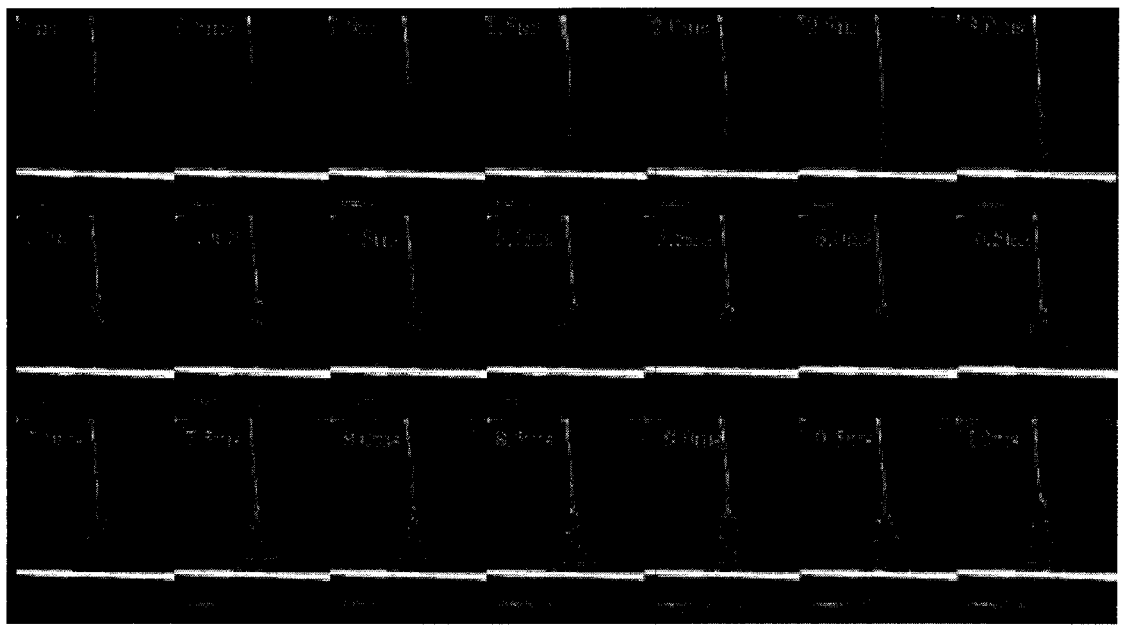
FIG. 25 is a series of images illustrating the formation of bending instability in an electrospinning jet.

The straight segment of the jet extends from the orifice to the collector when the voltage is set at 5.5 KV. Then after the second frame, the voltage is reduced in a short time to 5.4 KV. The reduced voltage leads to a thinner jet which has a lower bending stiffness. The electrical bending instability began to form about 36 mm below the orifice (FIG. 25, 0.5 ms). In 1.5 ms the instability is carried down to about 43 mm (FIG. 25, 2.0 ms). At 3.0 ms a new electrical bending instability occurs at about 30 mm (FIG. 25, 3.0 ms). At 4.5 ms, the coils of the first electrical bending instability are about to move out of the field of view. A new instability develops at about 30 mm (FIG. 25, 4.5 ms) and develops more fully. At 6.0 and 7.5 ms, the electrical bending instability starts at 30 mm and moves downward at a velocity of approximately 4 m/s (FIG. 25, 6.0 ms, 7.0 ms). From this series of images it is found that the frequency of the electrical bending instability is in the range of $10^3$ to $10^4$ Hz. If the voltage is increased to 5.5 KV, the onset of the electrical bending instability moves downward and the straight segment reaches to the collector.

that can determine the onset of buckling in a gravity driven jet. When the Reynolds number of the liquid is larger than about 1.2 the jet is stable and buckling does not occur. If the experimental fall height is less than the critical fall height, no buckling occurs. Folding and coiling are two kinds of buckling instabilities. Jets of circular cross-section first fold. At a greater length the same jet begins to coil. Planar jets (ribbons) only fold when they become unstable and buckle.

Figure 26:
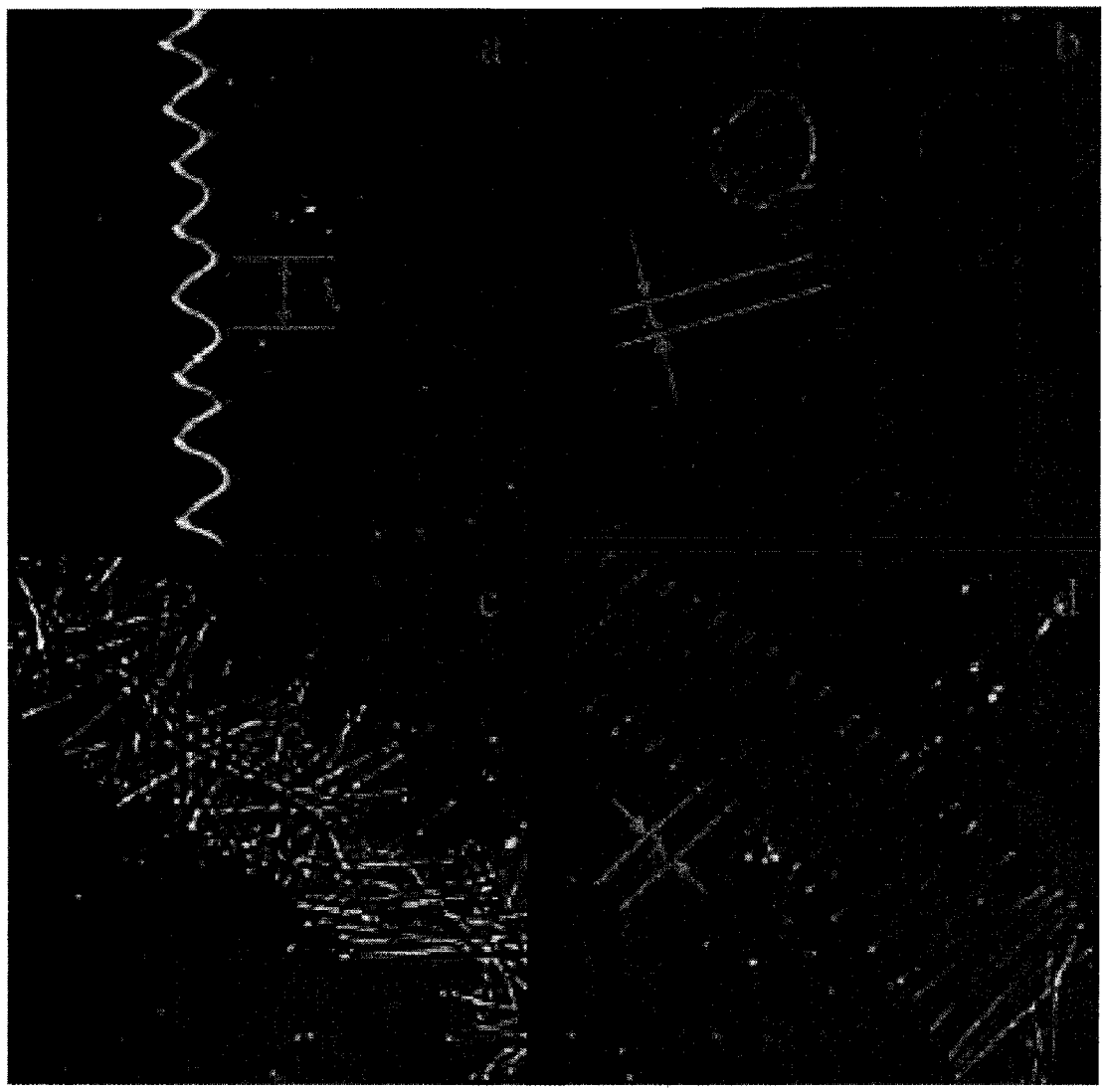
FIG. 26a through 26d are optical microscopic images of buckled electrospun PLLA fibers.

The PLLA solution, held in the spinneret, is connected to high voltage power supply. The inner diameter of the capillary is about 160 μm. The distance from the capillary orifice to the grounded collector is 20 mm. The collector is moved at 0.1 m/s. The voltage is 1500 V. Under these conditions, the electrical bending instability does not occur and only a straight path jet is observed. The buckled fibers collected on glass microscope slides are observed using optical microscopy. The amount of the charge carried by these fibers is quickly dissipated by the surface conductivity of the glass. FIG. 26 shows buckling phenomena observed in PLLA fibers made from the straight segment of an electrospinning jet. Sinuous folding, zigzag folding and helical coiling occurs. The wave lengths of buckles are about 6 to about 30 μm, although the present invention is not limited thereto. The frequencies are around $10^4$ Hz. See Table 1 for additional data.

The present invention illustrates that the buckling frequency of electrospinning jet is in the range of about $10^4$ to about $10^6$ Hz. The observed buckling frequency of an electrospinning jet is about 2 to 3 orders higher than the frequency associated with the electrical bending instability, which is in the range of $10^3$ Hz.

Figure 27:
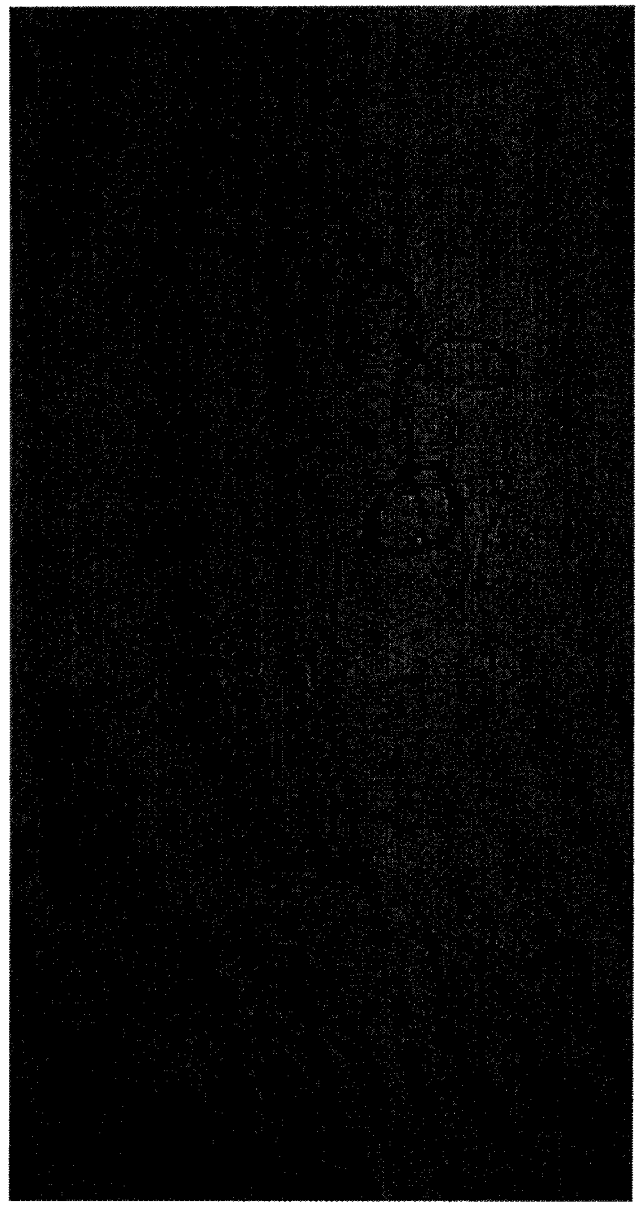

FIG. 27 is an image of a continuous electrospun PLLA fiber that buckled in several modes: coiled at the top, zigzag at the bottom and some transitional forms between. The length of the horizontal edge of the image is 0.7 mm.

Relationship Between Buckling and Bending Instabilities in an Electrospinning Jet:

A moving collector inclined by only 5 degree is used to collect one single electrospun nylon-6 fiber, which exhibits different morphologies formed at slightly different collector distances. Nylon 6 nanofibers are electrospun from an orifice at the orifice of a pipette that has an orifice diameter of 160 μm. The height of the column of solution above the orifice is about 3 cm, so the Hydrostatic pressure inside the orifice is about 200 Pa ($N/m^2$). The pressure does not change significantly during the experiment.

Figure 28:
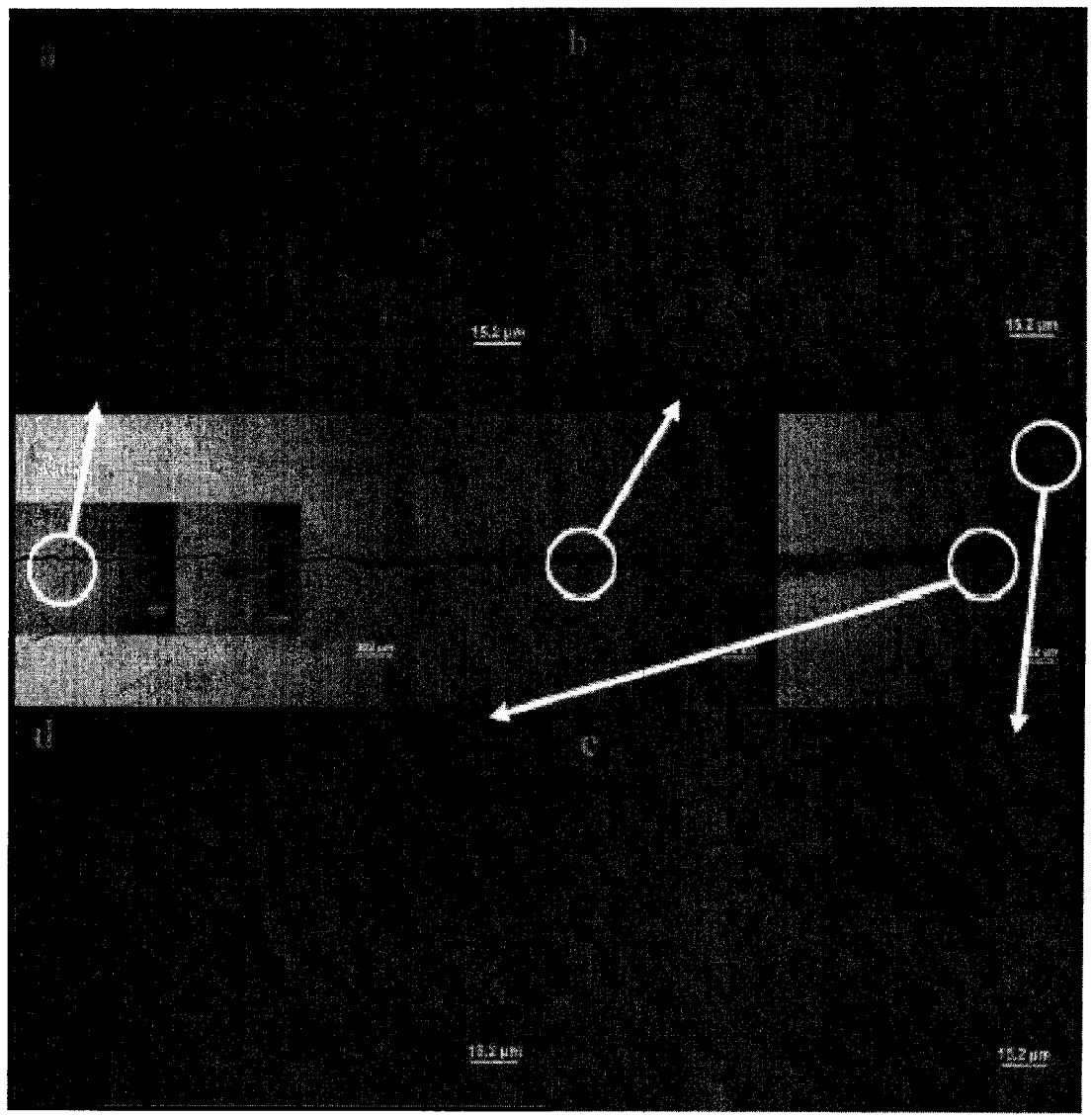
FIG. 28 is a series of images of buckled and bent electrospun Nylon 6.

FIG. 28 is a set of images of a buckled and bent electrospun nylon-6 fiber. The length of the horizontal edges of the images a, b, d, e are 0.18 mm; the length of the horizontal edge of the image c is 0.9 mm. See Table 1 for additional data.

The electrospun fiber, collected on the glass microscope slide, is observed with an optical microscope. Five images are fitted together to create the composite in FIG. 28c. The collection distance increases from about 1 mm to about 75 mm as the inclined collector is moved laterally. The nearly straight electrospinning jet forms a complex network of small loops that waver slightly, as shown at higher magnification in FIG. 28a. The second small block from the left edge of FIG. 28c details the onset of a bending instability coil with loops having relatively large diameters which gradually shrink and then expand to a diameter of over 200 μm at the location of the image in FIG. 28b. This image shows the presence of many 15 μm diameter coils formed by buckling that occurs when the jet is stopped on the collector. FIG. 28d shows similar buckling coils superimposed upon the larger diameter electrical bending coils typical of the region indicated by the tail of the arrow in the upper right corner. Near the right edge of FIG. 28c, even larger coils due to the electrical bending are observed. The enlarged image shown in FIG. 28e details coils and sinuous paths caused by buckling. The buckling instability occurs both before and after the electrical bending instability develops, and produces coils or sinuous features a little less than 15 μm in scale, near the region shown in FIG. 28a and a little more than 15 μm near the region shown in FIG. 28e. See Table 1 for additional data.

In light of the above, the present invention relate to structures that contain one or more fiber and/or nanofiber structures where such structures can be formed on a wide variety of structures or surfaces (e.g., asperties, flat surfaces, angled surface, hierarchical structures, etc.). In one embodiment, the present invention relates to a process for forming one or more fibers, nanofibers or structures made therefrom on a wide variety of structures or surfaces (e.g., asperities, flat surfaces, angled surface, hierarchical structures, etc.). In another embodiment, the present invention relates to a process for forming one or more fibers, nanofibers or structures made therefrom on a wide variety of structures or surfaces (e.g., asperities, flat surfaces, angled surface, hierarchical structures, etc.) where such fibers and/or structures are designed to sequester, carry and/or encapsulate one or more substances. In still another embodiment, the present invention relates to structures that contain one or more fiber and/or nanofiber structures on asperities where the nanofiber and/or fiber structures are designed to sequester, carry and/or encapsulate one or more substances.

In one embodiment, the present invention relates to methods for forming the above-mentioned structures using the electrical bending and mechanical buckling instabilities of an electrospinning jet as it is collected on a solid surface at a continuous series of distances from the orifice from which the jet emerges. These two instabilities may occur independently, or they may be superimposed. For example, a fluid loop of an electrical bending coil can buckle as it lands on the collector. The buckling always occurs close to the collector, and the diameter of the coils or the length folded segments produced by such buckling are much smaller than diameter of the coils produced by electrical bending of the same jet. The frequencies associated with mechanical buckling are from $10^2$ to $10^3$ times higher than the frequencies associated with the electrical bending instability.

As used herein the words and/or phrases, bent, bending instability, electrical bending instability, and electrically driven instability, all refer to the same class of behaviors of the jet. Whereas the words buckled and folded refer to a different class of behaviors which occur very close to the collector, or collecting surface. Both these classes of behavior can occur independently and can each be controlled, either independently or in conjunction with one another, to produce the wide variety of structures mentioned above.

In the broadest sense, the present invention permits the formation of fiber, or nanofiber, structures that have a given, or controlled, porosity, a large surface area to mass ratio, and/or are mechanically robust.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A nanofiber structure for injecting bioactive substances through the skin comprising:
    a base surface having at least one tapered pin thereon, said tapered pin being designed to pierce skin;
    an electrospun polymer collected as a bead at a tip of said at least one tapered pin, wherein the electrospun polymer contains at least one bioreactive substance therein that is released from the electrospun polymer upon contact with blood or bodily fluids.

2. The nanofiber structure of claim 1, wherein the at least one bioreactive substance is selected from the group consisting of drugs, pro-drugs, biologics, enzymes, hormones, antigens, antibodies, proteins, peptides, amino acids, dyes, fluorescent or phosphorescent compounds, diagnostic agents, therapeutic agents, color-change indicators, antibiotics, anesthetics, analgesics, anti-clotting agents, immunosuppressives, statins, birth control, nicotine, antidepressants, anti-anxiety drugs, antipsychotics, psychotropics and combinations thereof.

3. The nanofiber structure of claim 1, wherein the base surface includes an array of tapered pins and wherein each tapered pin contains thereon an electrospun polymer collected as a bead and containing at least one bioreactive substance.

4. The nanofiber structure of claim 1, wherein the electrospun polymer is selected from one or more polyethyleneimines, polyethylene oxides, polylactic acids, or a combination of two or more thereof.

* * * * *